US008932989B2

(12) United States Patent
Seul

(10) Patent No.: US 8,932,989 B2
(45) Date of Patent: Jan. 13, 2015

(54) SIEVING OF NUCLEIC ACID SAMPLES

(75) Inventor: Michael Seul, Basking Ridge, NJ (US)

(73) Assignee: Bioinventors & Entrepreneurs Network, LLC, Warren, NJ (US)

( * ) Notice: Subject to any disclaimer, the term of this patent is extended or adjusted under 35 U.S.C. 154(b) by 22 days.

(21) Appl. No.: 13/190,163

(22) Filed: Jul. 25, 2011

(65) Prior Publication Data

US 2013/0029855 A1     Jan. 31, 2013

(51) Int. Cl.
| | | |
|---|---|---|
| C40B 20/04 | (2006.01) | |
| C40B 30/04 | (2006.01) | |
| C12Q 1/68 | (2006.01) | |
| C40B 50/10 | (2006.01) | |
| C40B 50/16 | (2006.01) | |

(52) U.S. Cl.
CPC ............ *C40B 20/04* (2013.01); *C40B 50/10* (2013.01); *C40B 50/16* (2013.01); *C12Q 1/6858* (2013.01); *B01J 2219/00576* (2013.01); *B01J 2219/00592* (2013.01); *B01J 2219/00722* (2013.01); *B01J 2219/00725* (2013.01)
USPC .............. 506/4; 506/9; 435/6.11; 435/6.12; 536/24.3

(58) Field of Classification Search
USPC ........................................................ 435/6.11
See application file for complete search history.

(56) References Cited

U.S. PATENT DOCUMENTS

| | | | |
|---|---|---|---|
| 5,144,139 A | 9/1992 | Hillman et al. | |
| 6,114,179 A | 9/2000 | Lapierre et al. | |
| 6,352,828 B1 | 3/2002 | Brenner | |
| 7,081,339 B2 | 7/2006 | Slepnev | |
| 7,083,914 B2 | 8/2006 | Seul et al. | |
| 7,312,034 B2 | 12/2007 | Virgos et al. | |
| 7,368,246 B2 | 5/2008 | Slepnev et al. | |
| 7,387,887 B2 | 6/2008 | Wittwer et al. | |
| 7,445,893 B2 | 11/2008 | Slepnev | |
| 7,456,281 B2 | 11/2008 | Dujols | |
| 7,498,054 B2 | 3/2009 | Banerjee et al. | |
| 7,550,266 B2 | 6/2009 | Slepnev | |
| 7,635,565 B2 | 12/2009 | Hashmi et al. | |
| 7,635,566 B2 | 12/2009 | Brenner et al. | |
| 7,858,307 B2 | 12/2010 | Ho | |
| 7,871,770 B2 | 1/2011 | Ho | |
| 8,021,842 B2 | 9/2011 | Brenner et al. | |
| 2002/0025532 A1* | 2/2002 | Huang et al. ................... 435/6 | |
| 2005/0147998 A1 | 7/2005 | White et al. | |
| 2006/0269932 A1 | 11/2006 | Slepnev et al. | |
| 2007/0065864 A1 | 3/2007 | Korzheva et al. | |
| 2007/0072223 A1 | 3/2007 | Slepnev | |
| 2007/0077582 A1 | 4/2007 | Slepnev | |
| 2009/0075274 A1 | 3/2009 | Slepnev et al. | |
| 2009/0136951 A1 | 5/2009 | Hart et al. | |
| 2009/0233802 A1* | 9/2009 | Bignell et al. ................. 506/2 | |

FOREIGN PATENT DOCUMENTS

WO     WO 0131056     3/2001

OTHER PUBLICATIONS

Farrar, Kerrie and Iaiain S Donnison, "Construction and screening of BAC libraries made from *Brachypodium genomic* DNA," Jun. 28, 2007, Nature Protocols, vol. 2 No. 7, pp. 1661-1674.*
Clavijo, O.P., et al., "HLA-Cw*1701 is associated with two sub-Saharan African-derived HLA haplotypes: HLA-B*4201, DRB*03 and HLA-B*4202 without DRB1*03," 1999, Tissue Antigens, 54, pp. 303-306.*
Tyagi, Sanjay et al., "Molecular Beacons: Probes that Fluoresce upon Hybridization," Mar. 1996, Nature Biotechnology, 14, pp. 303-308.*
Reischl, Udo, "PCR-Based Cloning and Subsequnt Expression of Antigenic Proteins in *Escherichia coli*," Methods in Molecular Medicine (1998), 13 (Molecular Diagnosis of INfectious Diseases, pp. 157-168.*
Bosse, Yohan et al., "Identification of susceptibility genes for complex diseases using pooling-based genome-wide association scans," Jan. 29, 2009, Journal of Human Genetics, 125, pp. 305-318.*
Ye, Fei et al., "Fluorescent Microsphere-Based Readout Technology for Multiplexed Human Single Nucleotide Polymorhpism Analysis and Bacterial Identification," 2001, Human Mutation, 17, pp. 305-316.*
Vreeland, Wyatt N. et al., "Multiplexed, High-Throughput Genotyping by Single-Base Extension and End-Labeled Free-Solution Electrophoresis," Sep. 1, 2002, Analytical Chemistry, vol. 74 No. 17, pp. 4328-4333.*
Iannone, Marie et al., "Multiplexed Single Nucleotide Polymorphism Genotyping by Oligonucleotide Ligation and Flow Cytometry," 2000, Cytometry, 39, pp. 131-140.*
'Blood Grouping Reagent Anti-D' product information, Micro Typing Systems Inc. [online], [retrieved on Apr. 11, 2011]. Retrieved from the California Blood Bank Society website using the Internet <URL: http://www.cbbsweb.org/enf/attachments/mts_dmonopi.pdf>.
Cardoso et al, 1998 "Mini-pool screening by nucleic acid testing for hepatitis B virus, hepatitis C virus and HIV: preliminary results," Transfusion, 38(10): 905-907.

(Continued)

*Primary Examiner* — Christopher M Gross
*Assistant Examiner* — Christopher Reyes
(74) *Attorney, Agent, or Firm* — Drinker Biddle & Reath LLP

(57) ABSTRACT

A method of selecting nucleic acid samples from a plurality of nucleic acid samples based on desired alleles including the steps of performing a first reaction in a plurality of pools of the alleles to be identified to produce reaction products including a source tag identifying said each pool; pooling the pools to provide pooled pools; for each of the desired alleles to be identified, performing a second reaction using said reaction products to produce allele-specific second reaction products comprising a marker tag and a derived source tag; identifying said allele-specific second reaction products to select nucleic acid sample. In some embodiments, the first reaction may not be performed. A source tag sharing number "d" may be determined for each of the alleles. Alleles may be binned together.

30 Claims, 20 Drawing Sheets

(56) References Cited

OTHER PUBLICATIONS

Chattopadhyay, P.K., et al., 2006, "Quantum dot semiconductor nanocrystals for immunophenotyping by polychromatic flow cytometry," Nat Med. 12(8): 972-7. Epub Jul. 23, 2006, Abstract only.
Colas, P., 2008, "The eleven-year switch of peptide aptamers," Journal of Biology, 7:2.
Crawford, M., et al., 2003, "Peptide aptamers: Tools for biology and drug discovery," Briefings in Functional Genomics and Proteomics, 2 (1): 72-79.
Davis, J.A., et al., 2006, "Deterministic hydrodynamics: Taking blood apart," PNAS, 103(40):14779-14784.
Fawcett, T., 2006, "An introduction to ROC analysis," Pattern Recognition Letters 27: 861-874.
Gale, B.K. 'Bonding, Packaging and Sacrificial Processes' [online], 2001 [retrieved Apr. 11, 2011]. Retrieved from the Internet <URL: http://www.eng.utah.edu/~gale/mems/Lecture%2016a%20Bonding.pdf>.
Garcia, E.P., et al., 2005, "Scalable Transcriptional Analysis Routine—Mutiplexed Quantitative Real-Time Polymerase Chain Reaction Platform for Gene Expression Analysis and Molecular Diagnostics", Journal of Molecular Diagnostics, 7(4):444-454.
Hashmi et al., "A Flexible Array Format for Large-Scale, Rapid Blood Group DNA Typing", Transfusion, vol. 45, May 2005.
Herzenberg, L.A., et al., 2002, "The History and Future of the Fluorescence Activated Cell Sorter and Flow Cytometry: A View from Stanford," Clinical Chemistry 48(10): 1819-1827.
Kozlov, I.A., et al., 2004, "Efficient strategies for the conjugation of oligonucleotides to antibodies enabling highly sensitive protein detection," Biopolmers, 73(5): 621-30. Abstract only.
Lind and Kubista. Real-Time Immuno-PCR on the ICycler IQ™ System, Rev. A. [online], [retrieved on Apr. 4, 2011]. Retrieved from the Internet <URL: http://www.biocompare.com/Articles/ApplicationNote/1173//Real-Time-Immuno-PCR-On-The-ICycle-IQ-System-Rev-A.html>.
Niemeyer, C.M., et al., 2005, "Immuno-PCR: high sensitivity detection of proteins by nucleic acid amplification," Trends in Biotechnology, 23(4): 208-216.
Pasanen, P.A., et al., 1993, "Receiver operating characteristic (ROC) curve analysis of the tumour markers CEA, CA 50 and CA 242 in pancreatic cancer; results from a prospective study," Br. J. Cancer (1993), 67: 852-855.

'Pooled BVD PCR Testing, Appendix I' Molecular Diagnostics [online], Jun. 30, 2011 [retrieved Jul. 13, 2011]. Retrieved from <URL: http://abdc.vet.cornell.edu/docs/BVD_PCR_Pooled_Testing.pdf>.
Radisic, M. et al., 2006. "Micro- and nanotechnology in cell separation," International Journal of Nanomedicine: 1(1): 3-14.
Sacher et al., "Widmann's Clinical Interpretation of Laboratory Tests, 11$^{th}$ edition," F.A. Davis Company, Philadelphia, PA, 2000, chapter 1, pp. 3-7.
Sritharan, D. 'Size-based cell sorting by deterministic lateral displacement' Northeastern University, Chemical Engineering Master's Theses, Paper 8 [online], 2009 [retrieved Apr. 11, 2011]. Retrieved from the Internet <URL: http://hdl.handle.net/2047/d10019078>.
Stewart, C.C., et al., "Clinical Immunophenotyping by Flow Cytometry," Med TechNet Presentations [online], 1995 [retrieved Apr. 11, 2011]. Retrieved from the Internet <URL: http://www.medtechnet.com/public_pdf/mtc13.pdf>.
Tait Stevens, W., et al., 2008, "Introduction to BioArray Solutions' BeadChip Technology," Scientific Communications, ASHI Quarterly, Second Quarter [online], 2008 [retrieved Apr. 11, 2011]. Retrieved from the Internet <URL: http://www.immucor.com/bioarry/pdf/Introduction_to_BioArray_Solutions_BeadChip_Technology.pdf>.
'West Nile Virus-Procleix® WNV Assay—Summary Basis of Approval', Gen-Probe Incorporated [online], [retrieved on Apr. 11, 2011]. Retrieved from the US Food and Drug Administration using Internet <URL: http://www.fda.gov/downloads/BiologicsBloodVaccines/BloodBloodproducts/ApprovedProducts/LicensedProductsBLAs/BloodDonorScreening/InfectiousDisease/UCM090365.pdf>.
Won, J.I., et al., 2005, "Protein polymer drag—tags for DNA separations by end-labeled free-solution electrophoresis", Electrophoresis, 26: 2138-2148.
Zhao and Zhang, 2006, "Cellular mechanics study in cardiac myocytes using PDMS pillars array," Sensors and Actuators A: Physical, 125(2): 398-404.
Office Action mailed Aug. 30, 2012; U.S. Appl. No. 13/190,147.
Office Action mailed Aug. 31, 2012; U.S. Appl. No. 13/190,154.
Office Action mailed Mar. 28, 2013; U.S. Appl. No. 13/190,147.
Office Action mailed Mar. 27, 2013; U.S. Appl. No. 13/190,154.

* cited by examiner

From FIG. 3A (d) if source tag sharing number "d" is less than the maximum pool size, then performing the following step:
    (i) for each of the one or more desired alleles, performing a second reaction in the at least one pooled pool using said reaction products comprising said source tag to produce allele-specific second reaction products comprising a marker tag and a derived source tag, wherein said derived source tag is at least one of: said source tag, a copy of said source tag, or a copy of the complement of the source tag, and wherein said marker tag identifies an allele at a polymorphic site, and wherein said second reaction is in a pooled pool of said at least one pooled pool;
    otherwise if source tag sharing number "d" is equal to or greater than the maximum pool size, then perform the following step:
    (ii) for each of the alleles of the one or more desired alleles, performing a second reaction in each pool of the plurality of pools to produce allele-specific second reaction products comprising a marker tag, wherein said marker tag identifies an allele at a polymorphic site;

350

(e) if source tag sharing number "d" is less than the maximum pool size, then performing the following step:
    (i) identifying said allele-specific second reaction products by interrogating said derived source tag and said marker tag to identify which pooled pools of the at least one pooled pool includes at least one nucleic acid sample that has an allele of the one or more of desired alleles, thereby identifying which of the plurality of groups of nucleic acid samples includes a nucleic acid sample with at least one allele of the one or more desired alleles;
    otherwise if source tag sharing number "d" is equal to or greater than the maximum pool size, then perform the following step:
    (ii) identifying said allele-specific second reaction products by interrogating said marker tag to identify which pools of the plurality of pools includes at least one nucleic acid sample that has an allele of the one or more desired alleles, thereby identifying which of the plurality of groups of nucleic acid samples includes a nucleic acid sample with at least one allele of the one or more desired alleles;

From FIG. 3B 

(f) if there are one or more additional desired alleles, then selecting the nucleic acid samples of the identified groups from the plurality of nucleic acid samples, and repeating steps (a)-(e) with the selected nucleic acid samples as the plurality of nucleic acid samples, and the additional desired alleles as the one or more desired alleles, otherwise selecting the nucleic acid samples of the identified groups from the plurality of nucleic acid samples.
370

African American

| Blood Grp System | ISBT Design | Alleles | A | B | f | d(s) | | pwr of 2 | | MinFreq 0.001 | Cutoff (=C) 0.1800 | | | Max PoolSz 32 | |
|---|---|---|---|---|---|---|---|---|---|---|---|---|---|---|---|
| | 852 | 854 | 856 | 858 | 860 | 862 | 864 | 866 | 874→32 | 16 | 8 | 4 | 2 | 1 | |
| Kell | 6-KEL | K(1/2) | 0.01 | 0.99 | 0.01 | 9.8729 | 3 | 8 | | | K(1/2) | | | | |
| Lutheran | 5-LU | LU | 0.03 | 0.97 | 0.03 | 3.2577 | 1 | 2 | | | | | LU | | |
| Duffy | 8-FY | FY | 0.12 | 0.88 | 0.12 | 0.7762 | 0 | 1 | | | | | | FY | |
| MNSs | 2-MNS | GYPBS | 0.18 | 0.82 | 0.18 | 0.5000 | 0 | 1 | | | | | | GYPBS | |
| Duffy | 8-FY | GATA | 0.29 | 0.71 | 0.29 | 0.2897 | 0 | 1 | | | | | | GATA | |
| Dombrock | 14-DO | DO-793 | 0.31 | 0.69 | 0.31 | 0.2674 | 0 | 1 | | | | | | DO-793 | |
| MNSs | 2-MNS | GYPA | 0.48 | 0.52 | 0.48 | 0.1517 | 0 | 1 | | | | | | GYPA | |
| Kidd | 9-JK | JK | 0.72 | 0.28 | 0.72 | 0.3021 | 0 | 1 | | | | | | JK | |
| Hemoglobin S | | HbS173 | 0.948 | 0.052 | 0.948 | 1.8581 | 0 | 1 | | | | | | HbS173 | |
| Dombrock | 14-DO | DO-323 | 0.96 | 0.04 | 0.96 | 2.4307 | 1 | 2 | | | | | DO-323 | | |
| Dombrock | 14-DO | DO-350 | 0.96 | 0.04 | 0.96 | 2.4307 | 1 | 2 | | | | | DO-350 | | |
| Duffy | 8-FY | FY265 | 0.99 | 0.01 | 0.99 | 9.8729 | 3 | 8 | | | FY265 | | | | |
| Scianna | 13-SC | SC(1/2) | 0.998 | 0.002 | 0.998 | 49.5631 | 5 | 32 | SC(1/2) | | | | | | |
| Diego | 10-DI | DI (B/A) | 1 | 0 | 1 | 99.1758 | 6 | 32 | DI (B/A) | | | | | | |
| Colton | 15-CO | CO | 1 | 0 | 1 | 99.1758 | 6 | 32 | CO | | | | | | |
| Landsteiner Wiener | 16-LW | LW | 1 | 0 | 1 | 99.1758 | 6 | 32 | LW | | | | | 820 | |
| | | | | | | | | 810 | 4 | 0 | 2 | 0 | 3 | 7 | |

800 Caucasian

| 850 | 852 | 854 | 856 | 858 | 860 | 862 | 864 | 866 | 874 | 16 | 8 | 4 | 2 | 1 |
|---|---|---|---|---|---|---|---|---|---|---|---|---|---|---|
| Blood Grp System | ISBT Design | Alleles | A | B | f | d(s) | | pwr of 2 | 32 | | | | | |
| Kell | 6-KEL | K(1/2) | 0.03 | 0.97 | | 3.2577 | 1 | 2 | | | | | K(1/2) | |
| Lutheran | 5-LU | LU | 0.03 | 0.97 | | 3.2577 | 1 | 2 | | | | | LU | |
| MNSs | 2-MNS | GYPBS | 0.34 | 0.66 | | 0.2388 | 0 | 1 | | | | | | GYPBS |
| Dombrock | 14-DO | DO-793 | 0.37 | 0.63 | | 0.2148 | 0 | 1 | | | | | | DO-793 |
| Duffy | 8-FY | FY | 0.41 | 0.59 | | 0.1881 | 0 | 1 | | | | | | FY |
| Kidd | 9-JK | JK | 0.52 | 0.48 | | 0.1517 | 0 | 1 | | | | | | JK |
| MNSs | 2-MNS | GYPA | 0.57 | 0.43 | 0.43 | 0.1765 | 0 | 1 | | | | | | GYPA |
| Duffy | 8-FY | GATA | 0.95 | 0.05 | 0.05 | 1.9345 | 3 | 1 | | | | | | GATA |
| Duffy | 8-FY | FY265 | 0.99 | 0.01 | 0.01 | 9.8729 | 3 | 8 | | | | FY265 | | |
| Scianna | 13-SC | SC(1/2) | 0.994 | 0.006 | 0.006 | 16.4879 | 4 | 16 | | SC(1/2) | | | | |
| Hemoglobin S | | HbS173 | 0.998 | 0.002 | 0.002 | 49.5631 | 5 | 32 | HbS173 | | | | | |
| Colton | 15-CO | CO | 0.999 | 0.001 | 0.001 | 99.1758 | 6 | 32 | CO | | | | | |
| Dombrock | 14-DO | DO-323 | 1 | 0 | 0.001 | 99.1758 | 6 | 32 | DO-323 | | | | | |
| Dombrock | 14-DO | DO-350 | 1 | 0 | 0.001 | 99.1758 | 6 | 32 | DO-350 | | | | | |
| Diego | 10-DI | DI (B/A) | 1 | 0 | 0.001 | 99.1758 | 6 | 32 | DI (B/A) | | | | | |
| Landsteiner Wiener | 16-LW | LW | 1 | 0 | 0.001 | 99.1758 | 6 | 32 | LW | | | | | |
| | | | | | | | | 830 | 6 | 1 | 1 | 0 | 2 | 6 840 |

868 → MinFreq 0.001
870 → Cutoff (=C) 0.1800
872 → Max PoolSz 32

876 →

SIEVING OF NUCLEIC ACID SAMPLES

FIELD

The invention relates to methods of selecting nucleic acid samples from a plurality of nucleic acid samples based on one or more desired alleles and more specifically to selecting nucleic acid samples by grouping the nucleic acid samples based on a frequency of one or more desired alleles.

BACKGROUND

In the discussion of the background that follows, reference is made to certain structures and/or methods. However, the following references should not be construed as an admission that these structures and/or methods constitute prior art. Applicants expressly reserve the right to demonstrate that such structures and/or methods do not qualify as prior art.

Replacement human blood is vital to medical treatment. Many medical treatments including many surgical procedures would not be possible without the availability of donated blood to replace blood lost during such procedures or due to injuries.

One problem in supplying replacement blood is that it is perishable. Blood, contains cellular components, principally red blood cells ("erythrocytes"), platelets ("thrombocytes") and white blood cells ("leukocytes"), suspended in plasma. As soon as blood is collected, red cells within the blood may acquire "storage lesions," which may reduce the effectiveness of these cells to deliver oxygen to tissue. Moreover, freezing and thawing may damage cells and reduce their effectiveness. The blood may also acquire inflammatory factors, especially when white cells are allowed to remain. The blood may also contain infectious agents that may proliferate, especially when blood components are stored at room temperature as is the case for platelets. For these reasons, fresh blood is more effective and, in practice, is preferred over older blood. Regulatory agencies have set the time period for using red blood cells to 42 days after collection, and the time period for using platelets to five days (or 7 days provided special storage conditions are ensured), reflecting the risk of proliferation of bacteria as platelets are stored at room temperature. Expired blood components are no longer suitable for human use. In the United States of America, in 2006, approximately 400,000 units of 16.75 million units of red blood cells collected, and approximately 200,000 units of 1.810 million units of (single donor) platelets collected, expired before use.

Another problem in supplying replacement blood is that the replacement blood is typically matched to the recipient's blood type only with respect to an abbreviated blood type such as A+, AB−, or O−, indicating the presence ("A", "B" or "AB") or absence ("O") of the antigens within the ABO blood group system and the presence ("+") or absence ("−") (often determined by traditional "agglutination" methods) of the D antigen, a constituent of the RH blood group system. However, blood cells express a multiplicity of antigens. For example, red blood cells comprise dozens of antigens within 30 blood group systems defined to date by the International Society of Blood Transfusion. Any of the antigens, which are associated with molecules on cell surfaces of replacement blood cells, may cause the recipient's immune system to treat the replacement blood as foreign if the recipient's own blood cells do not have the same antigens as the replacement blood antigens. This, in turn, may lead to immune reactions and adverse clinical events. Adverse events may be mild and have no significant effect on the patient or may be severe and life threatening. In 2006, 72,000 adverse transfusion-related events were reported.

Determining the identity of individual antigens, or that of an entire set comprising an antigen profile, for recipient and for (donors of) replacement blood may be prohibitively time consuming and expensive; in the USA, routine antigen testing prior to red blood cell transfusion currently is limited to the principal antigens, A, B and D while platelet transfusion routinely proceeds without any antigen testing.

One way to avoid an immune system reaction is to determine the recipient's and prospective donors' antigen profiles (for cells to be transfused) and to select replacement blood on the basis of its antigen profile such that it does not appear foreign to the recipient's immune system. However, finding suitable, or "compatible", antigen profiles may require determining the antigen profile of many donor blood samples. Additionally, current methods for determining blood cell antigen profiles, especially the traditional methods of directly probing antigens associated with proteins on cell surfaces are time consuming and expensive. Reagents that are needed to directly probe the antigens are scarce and expensive, and often unlicensed, and current procedures are time-consuming with only one antigen at a time being determined. Additionally, there may be many technical difficulties encountered especially when analyzing complex cases for patients who are in need of transfusion.

An alternative method of determining antigen profiles directly relies on the analysis of a genomic DNA ("gDNA") sample by determining specific sequences of nucleotides within genes known to encode blood group antigens. Alternate forms of related sequences of nucleotides, also referred to as alleles, may encode alternate forms of an antigen, as in the case of many blood group antigens. A variable site within the sequence of nucleotides, also referred to as polymorphic site or a polymorphism, may be referred to as a marker, and the composition at that site an allele or attribute of the DNA (that is: a genetic attribute); determining one or more alleles or attributes of DNA may be called determining an allele or attribute profile of the DNA. So, determining an attribute profile of the DNA may also be called determining an allele profile of the DNA, and more generally determining an attribute profile or allele profile for a nucleic acid, since DNA is a nucleic acid.

In current practice, it is common to determine allele profiles one sample at a time, and often one allele at a time, and given the requisite expenditure of time, frequently many hours, even with state-of-the-art methods of "multiplex" analysis providing the entire allele profile of an individual, making it impractical to conduct comprehensive allele profiling of large numbers of individuals, including recipients or donors of blood. These same problems relating to transfusion may be common to problems where alleles of a nucleic acid must be determined, especially when large numbers of samples are to be processed rapidly and cost-effectively, for example, for the purpose of selecting units for transfusion on the basis of matching donor allele profiles to those of intended recipients. Similarly, it would be desirable to select individuals on the basis of desirable allele profiles and corresponding phenotypic stratification, for example, in connection with selecting participants for clinical trials in accordance with profiles relating to rates of drug metabolism.

SUMMARY

Therefore there is a need in the art for a method of selecting nucleic acid samples from a plurality of nucleic acid samples based on one or more desired alleles. The method may include step (a) dividing the plurality of nucleic acid samples into nucleic acid sample groups, each group containing approximately a source tag sharing number "d" nucleic acid samples so that each nucleic acid sample of the plurality of nucleic acid samples is included in at least one group. The source tag sharing number "d" may be a number determined based on a frequency of the one or more desired alleles. The method may include step (b) for each of the nucleic acid sample groups, placing a portion of each of the nucleic acid samples included in the nucleic acid sample group into a pool, thereby providing a plurality of pools. Each pool may comprise a pooled group of nucleic acid samples. The method may include a step (c) if source tag sharing number "d" is less than a maximum pool size, then performing step (i) and step (ii). Step (i) may include performing a reaction in each pool of the plurality of pools to produce reaction products comprising a source tag identifying said each pool. The reaction products may be produced using as templates said pooled group of nucleic acid samples in said each pool. Step (ii) may include pooling in at least one pooled pool at least some of the said produced reaction products from at least two pools of the plurality of pools, thereby providing at least one pooled pool. The method may include a step (d) if source tag sharing number "d" is less than the maximum pool size, then performing the following steps (i) and (ii). Step (i) may include for each of the alleles of the one or more desired alleles, performing a second reaction in the at least one pooled pool using said reaction products comprising said source tag to produce allele-specific second reaction products comprising a marker tag and a derived source tag. The derived source tag may be at least one of: said source tag, a copy of said source tag, or a copy of the complement of the source tag. The marker tag may identify an allele at a polymorphic site. The second reaction may be in a pooled pool of said at least one pooled pool. If source tag sharing number "d" is equal to the maximum pool size, then perform the following step (ii) for each of the alleles of the one or more desired alleles, performing a second reaction in each pool of the plurality of pools to produce allele-specific second reaction products comprising a marker tag. The marker tag may identify an allele at a polymorphic site. The method may include step (e) if source tag sharing number "d" is less than the maximum pool size, then performing the following step (i). Step (i) may include identifying said allele-specific second reaction products by interrogating said derived source tag and said marker tag to identify which pooled pools of the at least one pooled pool include at least one nucleic acid sample that has an allele of the one or more of desired alleles, thereby identifying which of the plurality of groups of nucleic acid samples includes a nucleic acid sample with at least one allele of the one or more desired alleles. If source tag sharing number "d" is equal to the maximum pool size, then the following step (ii) may be performed. Step (ii) may include identifying said allele-specific second reaction products by interrogating said marker tag to identify which pools of the plurality of pools includes at least one nucleic acid sample that has an allele of the one or more desired alleles, thereby identifying which of the plurality of groups of nucleic acid samples includes a nucleic acid sample with at least one allele of the one or more desired alleles; and (f) if there are one or more additional desired alleles, then selecting the nucleic acid samples of the identified groups from the plurality of nucleic acid samples, and repeating steps (a)-(e) with the selected nucleic acid samples as the plurality of nucleic acid samples, and the additional desired alleles as the one or more desired alleles, otherwise selecting the nucleic acid samples of the identified groups from the plurality of nucleic acid samples.

Step (f) may comprise if there are one or more additional desired alleles and source tag sharing number "d" is greater than "1", then selecting the nucleic acid samples of the identified groups from the plurality of nucleic acid samples, and repeating steps (a)-(e) with the selected nucleic acid samples as the plurality of nucleic acid samples, the additional desired alleles as the one or more desired alleles, and a lower source tag sharing number "d", otherwise selecting the nucleic acid samples of the identified groups from the plurality of nucleic acid samples.

The method may include binning the one or more desired alleles by determining a source tag sharing number "d" for the one or more desired alleles based on a frequency of the set of desired alleles.

Step (c) (i) may include amplifying the nucleic acid samples in the pool with primers comprising a source tag, and wherein said reaction products comprise amplicons.

Amplifying the nucleic acid samples may include amplifying the nucleic acid samples by performing a polymerase chain reaction (PCR).

Performing a second reaction may include amplifying said reaction products with allele-specific primers using said reaction products as templates. The allele-specific second reaction products may comprise allele-specific amplicons.

The allele-specific amplicons may indicate the identity of the allele of the allele-specific amplicon by a length of the allele-specific amplicon.

Amplifying the nucleic acid samples may include amplifying the nucleic acid samples by performing a polymerase chain reaction (PCR).

The marker tag of the second reaction products may include least one of the following to identify an allele: an oligonucleotide tag or a fluorescent tag.

The marker tag may include an oligonucleotide tag comprising a first nucleotide sequence to identify an allele and a second nucleotide sequence to identify a polymorphic site.

The oligonucleotide tag may include a nucleotide sequence to identify both a polymorphic site and said allele.

The marker tag of said second reaction products may include at least one of the following to identify a polymorphic site of the plurality of polymorphic sites: an oligonucleotide tag or a fluorescent tag.

Interrogating may include interrogating said derived source tag and said marker tag of said second reaction products by contacting said second reaction products with micro-particles, said micro-particles comprising a first capture probe complementary to said derived source tag and comprising an optical tag that identifies said micro-particle.

The micro-particles may include a second capture probe complementary to said marker tag, and wherein said marker tag is an oligonucleotide tag.

The marker tags may include an optical tag.

The optical tags may be a fluorescent tag.

Interrogating may include interrogating said derived source tag and said marker tag of said second reaction products by electrophoretic separation of said second reaction products.

Interrogating may include determining a length of the second reaction products by electrophoretic separation.

The marker tags may include an optical tag.

The source tag identifying said each pool may encode said each pool by a length of the source tag.

The marker tag may encode an identity of a polymorphic site by a length of the marker tag.

The identity of a polymorphic site may be encoded by the total length of said second reaction products.

The second reaction products may encode at least one of an allele or a polymorphic site.

The source tags may be a unique nucleotide sequence.

Identifying said allele-specific second reaction products may include: if said interrogating of said derived source tag and said marker tag indicates allele-specific second reaction products in the same pooled pool with different marker tags for a polymorphic site and "d"=1, then a nucleic acid sample of the plurality of nucleic acid samples corresponding to a pool identified by said derived source tag is identified as heterozygous for the polymorphic site.

Identifying said alleles of the plurality of polymorphic sites may include if said interrogating of said derived source tag and said marker tag indicates that all allele-specific second reaction products in the same pooled pool have the same marker tag for a polymorphic site and if "d">1, then each of the nucleic acid samples used to form said pooled pool have the allele identified by the marker tag.

The method may include binning the one or more desired alleles into one or more bins based on a frequency of said desired alleles. In step (d), the second reaction may be performed in a same pooled pool of said at least one pooled pool for each of the alleles grouped into a same bin of the plurality of bins. Two alleles may be binned into the same bin if the two alleles have the same source tag sharing number "d".

The marker tag may uniquely identify an allele at a polymorphic site.

The source tag sharing number "d" may be a number determined based on a frequency of the one or more desired alleles with the plurality of nucleic acid samples.

A method of identifying which groups of a plurality of groups of nucleic acid samples includes a nucleic acid sample with at least one allele of one or more desired alleles is disclosed. The method includes step (a) for each of the nucleic acid sample groups, placing a portion of each of the nucleic acid samples included in the nucleic acid sample group into a pool, thereby providing a plurality of pools. Each pool may comprise a pooled group of nucleic acid samples. The method may include step (b) for each pool of the plurality of pools, performing a reaction in the pool to produce reaction products comprising a source tag identifying said each pool. The reaction products may be produced using as templates said pooled group of nucleic acid samples in said each pool. The method may include step (c) pooling in at least one pooled pool at least some of the said produced reaction products from at least two pools of the plurality of pools, thereby providing at least one pooled pool. The method may include step (d) for each of the one or more desired alleles, performing a second reaction in the at least one pooled pool using said reaction products comprising said source tag to produce allele-specific second reaction products comprising a marker tag and a derived source tag. The derived source tag may be at least one of: said source tag, a copy of said source tag, or a copy of the complement of the source tag. The marker tag may identify an allele at a polymorphic site. The second reaction may be in a pooled pool of said at least one pooled pool. The method may include step (e) identifying said allele-specific second reaction products by interrogating said derived source tag and said marker tag to identify which pools of the at least one pooled pool includes at least one nucleic acid sample that has an allele of the one or more desired alleles, thereby identifying which of the plurality of groups of nucleic acid samples includes a nucleic acid sample with at least one allele of the one or more desired alleles.

The method may include generating the plurality of nucleic acid sample groups by dividing a plurality of nucleic acid samples into nucleic acid sample groups, each group containing approximately "d" nucleic acid samples so that each nucleic acid sample of the plurality of nucleic acid samples is included in at least one group. The "d" may be a number determined based on a frequency of the one or more desired alleles.

A method of identifying nucleic acid samples from a plurality of nucleic acid samples based on one or more desired alleles is disclosed. The method may include step (a) dividing the plurality of nucleic acid samples into nucleic acid sample groups, each group containing approximately a source tag sharing number "d" nucleic acid samples so that each nucleic acid sample of the plurality of nucleic acid samples is included in at least one group. The source tag sharing number "d" may be a number determined based on a frequency of the one or more desired alleles. The method may include step (b) for each of the nucleic acid sample groups, placing a portion of each of the nucleic acid samples included in the nucleic acid sample group into a pool, thereby providing a plurality of pools. Each pool may comprise a pooled group of nucleic acid samples. The method may include step (c) (i) performing a reaction in each pool of the plurality of pools to produce reaction products comprising a source tag identifying said each pool. The reaction products may be produced using as templates said pooled group of nucleic acid samples in said each pool. Step (c) may include (ii) pooling in at least one pooled pool at least some of the said produced reaction products from at least two pools of the plurality of pools, thereby providing at least one pooled pool. The method may include step (d) for each of the alleles of the one or more desired alleles, performing a second reaction in the at least one pooled pool using said reaction products comprising said source tag to produce allele-specific second reaction products comprising a marker tag and a derived source tag. The derived source tag may be at least one of: said source tag, a copy of said source tag, or a copy of the complement of the source tag. The marker tag may identify an allele at a polymorphic site. The second reaction may be in a pooled pool of said at least one pooled pool. The method may include (e) identifying said allele-specific second reaction products by interrogating said derived source tag and said marker tag to identify which pooled pools of the at least one pooled pool include at least one nucleic acid sample that has an allele of the one or more of desired alleles, thereby identifying which of the plurality of groups of nucleic acid samples includes a nucleic acid sample with at least one allele of the one or more desired alleles. The method may include step (f) if there are one or more additional desired alleles, then selecting the nucleic acid samples of the identified groups from the plurality of nucleic acid samples, and repeating steps (a)-(e) with the selected nucleic acid samples as the plurality of nucleic acid samples, and the additional desired alleles as the one or more desired alleles, otherwise selecting the nucleic acid samples of the identified groups from the plurality of nucleic acid samples.

Step (f) may comprise if there are one or more additional desired alleles and source tag sharing number "d" is greater than "1", then selecting the nucleic acid samples of the identified groups from the plurality of nucleic acid samples, and repeating steps (a)-(e) with the selected nucleic acid samples as the plurality of nucleic acid samples, the additional desired alleles as the one or more desired alleles, and a lower source tag sharing number "d", otherwise selecting the nucleic acid samples of the identified groups from the plurality of nucleic acid samples.

The method may include binning the one or more desired alleles by determining a source tag sharing number "d" for the one or more desired alleles based on a frequency of the set of desired alleles.

A method of selecting nucleic acid samples from groups of a plurality of groups of nucleic acid samples based on at least one allele of one or more desired alleles is disclosed. The method comprises the steps of (a) for each of the nucleic acid sample groups, placing a portion of each of the nucleic acid samples included in the nucleic acid sample group into a pool, thereby providing a plurality of pools, wherein each pool comprises a pooled group of nucleic acid samples; (b) for each pool of the plurality of pools, and for each of the one or more desired alleles, performing a reaction in the pool to produce allele-specific reaction products comprising a marker tag wherein said marker tag indicates an allele at a polymorphic site, and wherein said reaction products are produced using as templates said pooled group of nucleic acid samples in said each pool; (c) detecting the presence of at least one of said allele-specific reaction products by interrogating said marker tags to identify which pools of the plurality of pools include at least one nucleic acid sample that has an allele of the one or more desired alleles, thereby identifying which of the plurality of groups of nucleic acid samples includes a nucleic acid sample with at least one allele of the one or more desired alleles; and (d) selecting the nucleic acid samples of said identified groups of nucleic acid samples that include a nucleic acid sample with at least one allele of the one or more desired alleles.

The method of selecting nucleic acid samples from groups of a plurality of groups of nucleic acid samples may further comprise before step (a), a step of: generating the plurality of nucleic acid sample groups by dividing a plurality of nucleic acid samples into nucleic acid sample groups, each group containing approximately "d" nucleic acid samples so that each nucleic acid sample of the plurality of nucleic acid samples is included in at least one group, wherein "d" is a number determined based on a frequency of the one or more desired alleles and experimental considerations.

The method of selecting nucleic acid samples from groups of a plurality of groups of nucleic acid samples may further comprise after step (d) a step of: repeating steps (a)-(d) with one or more additional alleles as the one or more desired alleles.

BRIEF DESCRIPTION OF THE DRAWING

The following detailed description can be read in connection with the accompanying drawings in which like numerals designate like elements and in which:

FIGS. 3A, 3B, and 3C schematically illustrate a method of selecting nucleic acid samples from a plurality of nucleic acid samples based on one or more desired attributes;

FIGS. 8A and 8B schematically illustrates an example of determining the number "d" for a set of polymorphic sites with two sets of allele frequencies, one for an African American population (top), the other for a Caucasian population (bottom);

DETAILED DESCRIPTION

Figures 1A, 1B:
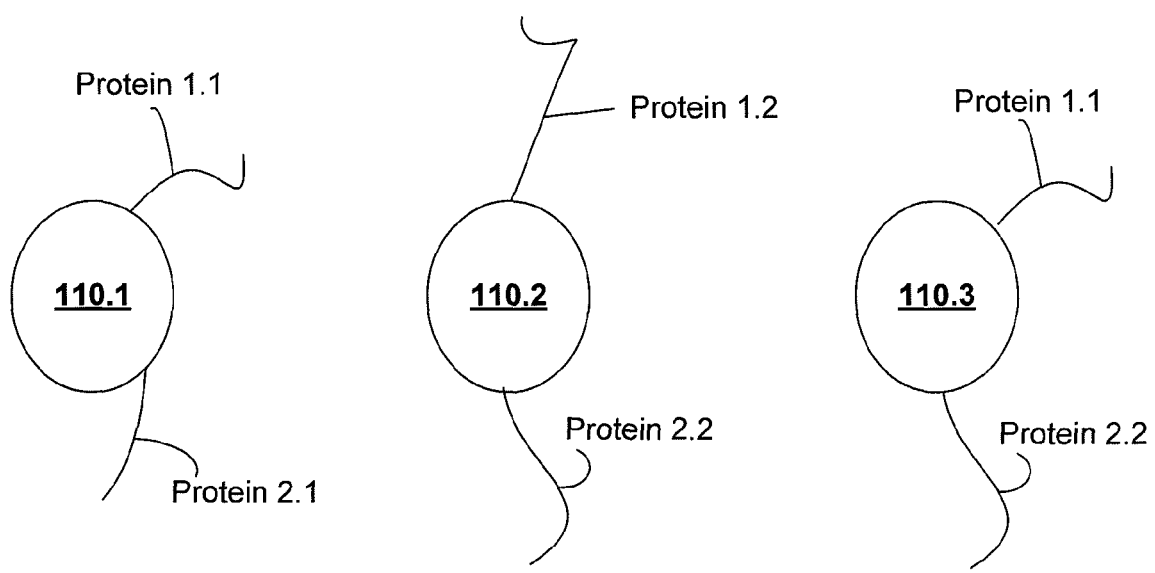
FIG. 1A schematically illustrates an allele profile for three DNA molecules, DNA-1, DNA-2, DNA-3, for two polymorphisms, polymorphism 1 and polymorphism 2.
FIG. 1B schematically illustrates blood cells with proteins attached on the blood cell surfaces, where the proteins are encoded by the DNA molecules of FIG. 1A.

It is to be understood that both the foregoing general description and the following detailed description are exemplary and explanatory and are intended to provide further explanation of the invention as claimed.

Unless otherwise defined, all technical and scientific terms used herein have the same meaning as commonly understood by one of ordinary skill in the art to which this invention belongs. Still, certain elements are defined for the sake of clarity and ease of reference.

DEFINITIONS

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

An "attribute" is a characteristic of a sample. Non-limiting examples of attributes include a gene allele and an antigen. Attribute characterization can include identifying a specific gene allele, identifying the presence of one or more of a set of antigens (such as blood antigens), identifying the presence or absence of a specific antigen, and identifying the relative amount of an antigen.

An "allele" refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variants", "polymorphisms", or "mutations".

An "allele-specific probe" is a probe that binds preferentially to a target nucleotide sequence comprising a certain allele at a polymorphic site in comparison to other alleles of the same polymorphism.

An "allele-specific primer" is a primer that binds preferentially to a target nucleotide sequence comprising a certain allele at a polymorphic site and provides for amplification of the allele in comparison to other alleles of the same polymorphism; elongation of an allele-specific primer produces a product complementary to the template sequence so that, if template sequences differ, in positions other than that targeted by the primer, so will the sequences of the elongation products, and in such a case, an allele-specific primer also may be referred to as a group-specific primer, the group comprising all alleles sharing the allele of the polymorphic site to which the primer is directed.

"Amplicon" means the product of a polynucleotide amplification reaction. That is, amplicons are a population of polynucleotides, usually double stranded, that are replicated from one or more starting sequences. The one or more starting sequences may be one or more copies of the same sequence, or may be a mixture of different sequences. Amplicons may be produced by a variety of amplification reactions whose products are multiple replicates of one or more target nucleic acids, that serve as templates for the addition of nucleobases in accordance with Watson-Crick base pairing rules. In one aspect, template-mediated reactions are primer extensions, catalyzed by a nucleic acid polymerase or template-mediated poly- or oligonucleotide ligations catalyzed by a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: U.S. Pat. Nos. 4,683,195; 4,965,188; 4,683,202; 4,800,159 (PCR); U.S. Pat. No. 5,210,015 (real-time PCR with "TAQMAN™" probes); U.S. Pat. No. 6,174,670; U.S. Pat. No. 5,399,491 ("NASBA"); U.S. Pat. No. 5,854,033 (rolling circle amplification). In one aspect, amplicons of the invention are produced by PCRs. As used herein, the term "amplifying" means performing (at least one cycle of—NOTE: a single primer "extension" or elongation pass without cycling of temperature may be sufficient in some embodiments) an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

An "allele-specific amplicon" means an amplicon that is the result of the template-mediated elongation of an allele-specific primer.

The term "complementary" refers to nucleic acid sequences comprising complementary base-pairs according to the standard Watson-Crick base-pairing, or that are capable of hybridizing to a particular nucleic acid segment under relatively stringent conditions.

The term "gene" refers to a nucleic acid (e.g., DNA) sequence that comprises coding sequences necessary for the production of a polypeptide, precursor, or RNA (e.g., rRNA, tRNA). The term "gene" encompasses both cDNA and genomic forms of a gene.

A "genome" is all the genetic material of an organism. In some instances, the term genome may refer to the chromosomal DNA. Genome may be multichromosomal such that the DNA is cellularly distributed among a plurality of individual chromosomes. For example, in human there are 22 pairs of chromosomes plus a gender associated XX or XY pair. DNA derived from the genetic material in the chromosomes of a particular organism is genomic DNA. The term genome may also refer to genetic materials from organisms that do not have chromosomal structure. In addition, the term genome may refer to mitochondria DNA.

The term "genotyping" refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be an A in some individuals and a C in other individuals. Those individuals who have an A at the position have the A allele and those who have a C have the C allele. A polymorphic location may have two or more possible alleles and oligonucleptide probes or primers may be designed to distinguish between all possible combinations.

The term "hybridization" refers to the process in which two single-stranded nucleic acids bind non-covalently to form a double-stranded nucleic acid; triple-stranded hybridization is also possible under certain conditions. Complementary sequences in the nucleic acids pair with each other to form a double helix. The resulting double-stranded nucleic acid is a "hybrid." Hybridization may be between, for example two complementary or partially complementary sequences. The hybrid may have double-stranded regions and single stranded regions. The hybrid may be, for example, DNA:DNA, RNA:DNA or DNA:RNA. Hybrids may also be formed between modified nucleic acids. One or both of the nucleic acids may be immobilized on a solid support. Hybridization techniques may be used to detect and isolate specific sequences, measure homology, or define other characteristics of one or both strands.

"Hybridization probes" are oligonucleotides capable of binding in a base-specific manner to a complementary strand of nucleic acid. Such probes include peptide nucleic acids, as described in Nielsen et al., 1991, Science 254, 1497-1500, and other nucleic acid analogs and nucleic acid mimetics. See U.S. Pat. No. 6,156,501.

"Ligation" means to form a covalent bond or linkage between the termini of two or more nucleic acids, e.g. oligonucleotides and/or polynucleotides, in a template-mediated reaction. The nature of the bond or linkage may vary widely and the ligation may be carried out enzymatically or chemically. A variety of template-mediated ligation reactions are described in the following references, which are incorporated by reference: U.S. Pat. No. 4,883,750; U.S. Pat. No. 5,476,930; U.S. Pat. No. 5,593,826; U.S. Pat. No. 5,426,180; U.S. Pat. No. 5,871,921.

A "label" is a composition detectable by spectroscopic, photochemical, biochemical, immunochemical, or chemical means. For example, useful labels include fluorescent dyes, electron-dense reagents, enzymes (e.g., as commonly used in an ELISA), biotin, digoxigenin, or haptens and proteins for which antisera or monoclonal antibodies are available. The label may be bound, either covalently or non-covalently, to a molecule. For example, a label may be bound to a tag and/or a ligand that binds a molecule or a tag, and more than one type of label can be bound to either or both of the tag and ligand. Thus, for example, an oligonucleotide tag can be covalently bound to a biotin group, where the oligonucleotide tag is then bound to a ligand that has a fluorescent label attached to the ligand.

As used herein, "nucleic acid" may include any polymer or oligomer of pyrimidine and purine bases, preferably cytosine, thymine, and uracil, and adenine and guanine, respectively. (See Albert L. Lehninger, Principles of Biochemistry, at 793-800 (Worth Pub. 1982), the entire disclosure of which is incorporated herein by reference.) Indeed, the invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

A single nucleotide polymorphism ("SNP") is a single position in a particular DNA sequence characterized by the presence in a population of two, three or four different nucleotides at that position. As is well known in the art, the position refers to a base pair. Therefore, the identity of a SNP allele can be accomplished by identifying the nucleotide on the sense strand or its base-paired complement on the antisense strand of a double-stranded DNA molecule.

An "oligonucleotide" or "polynucleotide" is a nucleic acid ranging from at least 2, preferably at least 8, 15 or 25 nucleotides in length, but may be up to 50, 100, 1000, or 5000 nucleotides long or a compound that specifically hybridizes to a polynucleotide. Polynucleotides include sequences of deoxyribonucleic acid (DNA) or ribonucleic acid (RNA) or mimetics thereof which may be isolated from natural sources, recombinantly produced or artificially synthesized. A further example of a polynucleotide may be a peptide nucleic acid (PNA). (See U.S. Pat. No. 6,156,501 the entire disclosure of which is incorporated herein by reference.)

The term "polymorphism" refers to the occurrence of two or more genetically determined alternative sequences or alleles in a population. A polymorphic marker or site is the locus at which divergence occurs. A polymorphism may comprise one or more base changes, an insertion, a repeat, or a deletion. A polymorphic locus may be as small as one base pair. The first identified allelic form is arbitrarily designated as the reference form and other allelic forms are designated as alternative or variant alleles. The allelic form occurring most frequently in a selected population is sometimes referred to as the wildtype form. A di-allelic or bi-allelic polymorphism has two forms. A triallelic polymorphism has three forms.

As used herein, a "pool" refers to a physical mixture comprising a portion of two or more biological samples. A "pooled pool" refers to a physical mixture comprising a portion of each of two or more different pools.

"Polynucleotide" and "oligonucleotide" are used interchangeably in this disclosure.

A "primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally-occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers may be labeled with, e.g., detectable moieties, such as chromogenic, radioactive or fluorescent moieties, or moieties for isolation, e.g., biotin. In some embodiments, complementarity of the primer's 3' terminal base and the template is a necessary condition for primer extension or elongation.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

As used herein a "probe" or "capture probe" is defined as a nucleic acid capable of binding to a target nucleic acid of complementary sequence by one or more types of chemical interactions, usually complementary base pairing mediated by hydrogen bond formation. As used herein, a probe may include natural (i.e., A, G, U, C, or T) or modified bases (7-deazaguanosine, inosine, etc.) forming an oligomer by way of phosphodiester or other bonds that do not interfere with hybridization. Thus, probes may be peptide nucleic acids in which the constituent bases are joined by peptide bonds rather than phosphodiester linkages.

"Sample" or "biological sample" as used herein means a biological material isolated from an individual. The biological sample may contain any biological material suitable for detection, and may comprise cellular and/or non-cellular material obtained from the individual. A "nucleic acid sample" is a sample comprising nucleic acid, in any degree of purity.

The term "tag" refers to a molecule or portion thereof with a recognizable feature that allows it to be distinguished from other tag molecules, e.g., a distinguishable nucleotide or amino acid sequence, nucleotide or amino acid sequence length, shape, size, mass, color, optical density, differential absorbance or emission of light, chemical reactivity, magnetic or electronic properties and the like. Preferred examples of tags include tags comprising oligonucleotides (oligonucleotide tags) and fluorescers. A specific oligonucleotide tag may serve to identify a sample or sequence, in the manner of a "barcode". A "tag" may include a florescent label so that the tag may be identified.

A "source tag" is a tag that is attached to or comprises a polynucleotide or oligonucleotide and identifies the source of the polynucleotide or oligonucleotide or nucleic acid under study. In some embodiments, a source tag is an "oligonucleotide tag". Oligonucleotide tags may be identified by their nucleotide sequences. In some embodiments the oligonucleotide tag is a sequence of nucleotides selected such that the sequence does not duplicate a naturally occurring sequence in the genome of the organism under study; such an oligonucleotide tag also is referred to as a "barcode"

A "marker tag," as used herein, is a tag that uniquely identifies a polymorphic site and/or allele. In some embodiments, the marker tag is the length of the "second" reaction products, which are defined below. In some embodiments, a marker tag is a tag that is attached to or comprises a polynucleotide or oligonucleotide and identifies an allele and/or polymorphic site under study. In some embodiments, a marker tag is an "oligonucleotide tag." Oligonucleotide tags may be identified by their unique nucleotide sequences and are "barcodes." In some embodiments, the marker tag may identifies an allele and/or polymorphic site under study by the length of the oligonucleotide tag. In some embodiments, the marker tag may identify an allele and/or polymorphic site by a fluorescent label.

The term "target" as used herein refers to a molecule that has an affinity for a given probe, or a segment of a particular molecule that has affinity for a probe. Targets may be naturally-occurring or man-made molecules. Examples of targets which can be employed by this invention include, but are not restricted to oligonucleotides and nucleic acids. A "target sequence" is a specific sequence of nucleotides of a target which is bound by a probe.

"Target nucleic acid" or "template nucleic acid sequence" or "target nucleotide sequence" refers to a region of a nucleic acid that is to be either replicated, amplified, and/or detected, generally including the flanking sequences to which primers may be directed By "reaction product" produced from a nucleic acid template is meant an amplification product, a transcription product, a reverse-transcription product, or any other nucleic acid product resulting from template-mediated nucleic acid synthesis.

The term "interrogating" as used herein refers to performing a process on reaction products that can be used to identify said reaction products in order to produce results that may be used to identify one or more alleles at one or more polymorphic site for one or more nucleic acid samples.

The term "unambiguous results" as used herein refers to results that can be used to determine an allele at a polymorphic site for a nucleic acid. The term "result" as used herein refers to an outcome of interrogating reaction products.

The term "ambiguous results" as used herein refers to results that require additional steps in order to determine an allele at a polymorphic site for a nucleic acid; in some embodiments two or more possible alleles, of two or more samples within a reaction, may have produced the same results.

As envisioned in the present invention with respect to the disclosed methods and compositions of matter, in one aspect the embodiments of the invention comprise the components and/or steps disclosed therein. In another aspect, the embodiments of the invention consist essentially of the components and/or steps disclosed therein. In yet another aspect, the embodiments of the invention consist of the components and/or steps disclosed therein.

The invention contemplates sample preparation methods in certain embodiments. Prior to or concurrently with the methods of genetic analysis described herein, the information comprising a nucleotide sequence in a sample for analysis may be amplified using a variety of mechanisms, some of which may employ polymerase chain reaction (PCR). See, for example, PCR Technology: Principles and Applications for DNA Amplification (Ed. H. A. Erlich, Freeman Press, New York, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965, 188, and 5,333,675, each of which is incorporated herein by reference in their entireties for all purposes.

Other suitable amplification methods include the ligase chain reaction (LCR) (for example, Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed PCR (CP-PCR) (U.S. Pat. No. 4,437, 975), arbitrarily primed PCR (AP-PCR) (U.S. Pat. Nos. 5,413,909, 5,861,245), degenerate oligonucleotide primed PCR (DOP-PCR) (Wells et al., 1999, Nuc Acids Res 27:1214-1218) and nucleic acid based sequence amplification (NABSA). (See, U.S. Pat. Nos. 5,409,818, 5,554,517, and 6,063,603, each of which is incorporated herein by reference). Other amplification methods that may be used are described in, U.S. Pat. Nos. 5,242,794, 5,494,810, 4,988,617 and in U.S. Ser. No. 09/854,317, each of which is incorporated herein by reference.

In certain aspects of the invention, nucleic acids are detected by detecting one or more tags (also referred to as labels) attached to a sample nucleic acids or to molecules that bind to nucleic acids. The tag or label may be incorporated by any of a number of means well known to those of skill in the art. In some embodiments, the tag is simultaneously incorporated during the amplification step in the preparation of the sample nucleic acids. Thus, for example, PCR with labeled primers or labeled nucleotides will provide a labeled amplification product. In other embodiments, transcription amplification, as described above, using a labeled nucleotide (e.g. fluorescein-labeled UTP and/or CTP) incorporates a label into the transcribed nucleic acids.

Alternatively, a tag may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example, nick translation or end-labeling (e.g. with a labeled RNA) by kinasing the nucleic acid and subsequent attachment (ligation) of a nucleic acid linker joining the sample nucleic acid to a label (e.g., a fluorophore).

Detectable tags suitable for use in the invention include any composition detectable by spectroscopic, photochemical, biochemical, immunochemical, electrical, optical or chemical means. Useful tags in the invention include, but are not limited to: biotin for staining with labeled streptavidin conjugate; anti-biotin antibodies, magnetic beads (e.g., Dynabeads™); fluorescent dyes (e.g., fluorescein, texas red, rhodamine, green fluorescent protein, and the like); radiolabels (e.g., $^{3}H$, $^{125}I$, $^{35}S$, $^{4}C$, or $^{32}P$); phosphorescent labels; enzymes (e.g., horse radish peroxidase, alkaline phosphatase and others commonly used in an ELISA); and colorimetric labels such as colloidal gold or colored glass or plastic (e.g., polystyrene, polypropylene, latex, etc.) beads. Patents teaching the use of such labels include U.S. Pat. Nos. 3,817,837, 3,850,752, 3,939,350; 3,996,345, 4,277,437, 4,275,149 and 4,366,241, each of which is hereby incorporated by reference in its entirety for all purposes.

Means of detecting such labels are well known to those of skill in the art. Thus, for example, radiolabels may be detected using photographic film or scintillation counters; fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

In some embodiments, the label comprises a microparticle that may be color-encoded, such as described in U.S. Pat. No. 7,083,914, the entire disclosure of which is incorporated herein by reference. Color codes are assigned for the purpose of uniquely labeling members of a group of microparticles to preserve their chemical identity thus the identity of microparticle-coupled nucleic acid. Color codes are based on a set of encoding fluorophores of distinguishable wavelengths, excited-state lifetimes and levels of intensity, the latter controlled by adjusting the abundances of dyes. The codes are interrogated to identify the bound nucleic acid.

In some embodiments, polynucleotide hybridization assays are conducted. Hybridization assay procedures and conditions will vary depending on the application and are selected in accordance with the general binding methods known including those referred to in: Maniatis et al. Molecular Cloning: A Laboratory Manual (2.sup.nd Ed. Cold Spring Harbor, N.Y., 1989); Berger and Kimmel, Methods in Enzymology, Vol. 152, Guide to Molecular Cloning Techniques (Academic Press, Inc., San Diego, Calif., 1987); Young and Davism, Proc. Natl. Acad. Sci USA, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

In some embodiments, signal detection of hybridization between ligands is used. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Ser. No. 10/389,194 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in PCT Application PCT/US99/06097 (published as WO99/47964), each of which also is hereby incorporated by reference in its entirety for all purposes.

In some embodiments of the invention, the source tags utilized in the practice of the invention comprise oligonucleotide tags. Usually, an oligonucleotide tag is attached to the 3'- or 5'-end of the a polynucleotide, or is incorporated into a reaction product, e.g. polymerase reaction product, which uses the polynucleotide as a template. Oligonucleotide tags may vary widely in size and compositions; the following references provide guidance for selecting sets of oligonucleotide tags appropriate for some embodiments. See U.S. Pat. No. 5,635,400; Brenner et al., Proc. Natl. Acad. Sci., 97: 1665-1670 (2000); European patent publication 0 303 459; Shoemaker et al., Nature Genetics, 14: 450-456 (1996); European patent publication 0799897A1; and U.S. Pat. No. 5,981, 179; the entire disclosures of which are incorporated herein by reference. In one aspect, oligonucleotide tags can each have a length within a range of from 2 to 36 nucleotides, or from 4 to 30 nucleotides, or from 8 to 20 nucleotides, respectively. A set of oligonucleotide tags may have a size in the range of from several tens to many thousands, or even millions. Preferably, the nucleotide sequence of the oligonucleotide tag is a sequence selected such that it is distinguishable from human genomic sequences, i.e., the oligonucleotide tags comprise barcodes.

As will be appreciated by those in the art, the attachment, or joining, of an oligonucleotide tag to a polynucleotide can be done in a variety of ways. In some embodiments, the sequence of the oligonucleotide tag is incorporated into the nucleotide sequence of primers of the reaction (extension primers, amplification primers, readout probes, genotyping primers, Rolling Circle primers, etc.) during the chemical synthesis of the primers. The tag then is incorporated in the reaction product formed in a primer-extension reaction, i.e., polymerase chain reaction, to form reaction product that now contains the tag sequence. Alternatively, the tag sequences can be added enzymatically. Furthermore, the tag can be attached to the target after synthesis; this post-synthesis attachment can be either covalent or non-covalent.

An oligonucleotide tag may be joined to a polynucleotide by a ligation method, i.e., formation a covalent bond or linkage between the termini of the oligonucleotide tag and polynucleotide in a template-driven reaction. The nature of the bond or linkage may vary widely and the ligation may be carried out enzymatically or chemically. A variety of template-driven ligation reactions are described in the following, which are incorporated by reference: Whitely et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al., Methods in Enzymology, 68: 50-71 (1979); Engler et al., The Enzymes, 15: 3-29 (1982); and Namsaraev, U.S. patent publication 2004/0110213.

In some embodiments, electrophoretic tags, or "e-tags" are used as source tags or marker tags, that are incorporated into nucleic acid molecules, such as described in U.S. Pat. No. 7,312,034, the entire disclosure of which is incorporated by reference. In practicing the method, target sequences are mixed with (i) a set of forward universal e-tag primers, each containing (i) a target sequence that is complementary to one of the known selected target sequences, and an extension sequence which is unique to the target sequence of that member, (ii) one or more reverse universal e-tag primers that are complementary to said target sequences, and (iii) enzyme and nucleotide components of a primer extension reaction, to form a target-sequence reaction mixture. The mixture is first reacted under primer extension reaction conditions, to form extended, preferably amplified target sequences. The extended target sequences are then reacted under hybridization conditions with a set of electrophoretic tag (e-tag) probes, each having (i) an oligonucleotide target-binding portion or moiety that is complementary to one of the extension sequences, (ii) an electrophoretic probe having separation characteristics, e.g., electrophoretic mobility, that is unique to a given extension sequence, and (iii) a linker joining the oligonucleotide portion and the electrophoretic probe, where the linker is cleavable under selected conditions when the oligonucleotide portion of the probe is bound to a complementary target extension sequence. The target sequences with bound probes are treated under the selected conditions, to release an e-tag reporter from each e-tag probe bound to a target sequence, the released reporters are separated, e.g., electrophoretically, and the separated reporters are detected, to identify target sequences that hybridized to the probes.

In some embodiments, tags and/or labels may be attached to solid phase supports, e.g., microparticles. Molecules such as oligonucleotides, proteins, aptamers and small organic molecules may be coupled to microparticles in accordance with any of the known coupling reactions in the art. See e.g., G. T. Hermanson, Bioconjugate Techniques (Academic Press, 1996) and Ilium et al., Methods in Enzymology 112: 67-84 (1985), the entire disclosures of which are incorporated herein by reference.

In some embodiments, allele-specific second reaction products are interrogated by differential melting curve analysis. This approach includes a fluorescent DNA dye, such as LCGreen® (Idaho Technology, Inc, Salt Lake City, Utah) designed to detect heteroduplexes, in a PCR amplification process to produce allele-specific second reaction products comprising the dye. The second reaction products are then subjected to melting analysis, preferably high resolution melting analysis, which involves generating a melting curve by measuring fluorescence from the DNA dye as the mixture is heated. Analysis of the melting curve identifies the alleles present based on melting temperature and melting curve shape. See, e.g., Wittwer et al., U.S. Pat. No. 7,387,887 and Dujols, U.S. Pat. No. 7,456,281, the entire disclosures of which are incorporated herein by reference. High resolution melting of small amplicons is also described in Liew et al., Clinical Chemistry 50:7 (2004), the entire disclosure of which is incorporated herein by reference. In these embodiments, the source tag, when present, may be identified by its contribution to at least the melting temperature $T_m$ of an amplicon.

In some embodiments, interrogation of reaction products may include both differential melting curve analysis and fragment size analysis.

A "maximum pool size" is a size that is approximately the maximum total number of biological samples that are or can be pooled together for reactions in the method. The "maximum pool size" may be determined by limitations arising from the steps of the method. For example, in some embodiments, two microparticles with different tags are added to a pool to identify alleles of a single nucleic acid sample. Thus, the number of nucleic acid samples that are pooled together is limited by the number of different microparticle tags that can be manufactured. The "maximum pool size" may be different for different reactions performed in the method, and the "maximum pool size" may be adjusted so that the method is efficient. In general, the "maximum pool size" is an indication of physical limits of the reactions that are performed in the method, but may be adjusted to more efficiently perform the method.

"Partitioning attributes" generally means to segment or sort attributes into one or more different bins, which may be referred to as groups, categories, or subsets, based on the frequency of the attributes. Bins may have a source tag number "d" associated with the bin. Attributes sorted into the same bin may be said to be "binned."

"Group testing" refers to identifying one or more specific attributes in a common mixture comprising a plurality of biological samples.

Some embodiments of the method include selecting nucleic acid samples from a plurality of nucleic acid samples based on a set of one or more desired alleles.

Relationship Between Blood Cell Proteins and DNA

FIG. 1A illustrates an allele profile 100 for three DNA molecules, DNA-1, DNA-2, DNA-3, for two polymorphisms, polymorphism 1 and polymorphism 2. The DNA molecules are listed along the vertical axis and the polymorphisms are listed along the horizontal axis. An allele profile 100 is an indication of which alleles are present in the DNA molecules at each of a number of polymorphisms. In FIG. 1A, there are two polymorphisms each with two different alleles. The allele profile for each of the DNA molecules, DNA-1, DNA-2, DNA-3, includes which nucleotide is present for each of the two polymorphisms. For example, referring to FIG. 1A, DNA-2, has nucleotide "G" for polymorphism 1 and nucleotide "T" for polymorphism 2. For ease of illustration, only the case where both chromosomes of the DNA, DNA-1, DNA-2, DNA-3, have the same nucleotide for the polymorphism has been illustrated, but, in general, the pair of chromosomes of the DNA, DNA-1, DNA-2, DNA-3, may have different nucleotides for the polymorphisms. For example, DNA-2 could have one chromosome with nucleotide "G" for polymorphism 1, and the other chromosome could have nucleotide "T" for polymorphism 1, in which case DNA-2 would be heterogeneous for polymorphism 1 rather than homozygous for polymorphism 1. Another name for an "allele profile" 100 is an "attribute profile" 100 of a nucleic acid molecule, since an allelic variation is an attribute of a nucleic acid molecule.

FIG. 1B illustrates blood cells with proteins attached on the blood cell surfaces, where the proteins are encoded by the DNA molecules of FIG. 1A. The notation "1.2" means the protein labeled with "1.2" was synthesized from an mRNA encoding polymorphism "1" with allele "2." As discussed above, the proteins may be antigens. The sequences of nucleotides G, A, T, and C of strands of the DNA, DNA-1, DNA-2, DNA-3, are used by the organism to synthesize the proteins 1.1, 1.2, 2.1, 2.2. Triplets of nucleotides (G, A, T, and C) encode an amino acid, and the amino acids are bonded together to form the proteins 1.1, 1.2, 2.1, and 2.2.

So, determining the allele or nucleotide at polymorphism 1 can be used to infer which protein 1.1 or 1.2 will be attached to a blood cell 110 produced by the organism.

The case of a single nucleotide (G, A, T, and C) difference at a polymorphism 1, 2 of the DNA molecule has been illustrated with only two different nucleotides possible at each polymorphism. This case is called a di-allelic or bi-allelic polymorphism. Note that blood cells were illustrated in FIG. 1B, but that determining alleles may also be used to infer the antigens of other cells such as red cells, platelets and leukocytes.

As discussed above, one use of allele profiling is to determine the identity of antigens associated with proteins, such as protein 1.1, protein 2.1, protein 1.2, protein 2.2, on surfaces of blood cells 110, which are synthesized from the corresponding DNA-1, DNA-2 or DNA-3 encoding the proteins. In particular, the comparison of allele profiles of candidate blood donors with the allele profile of a recipient of blood may be used to determine whether or not the proteins 1.1, 1.2, 2.1, 2.2 on the blood cells 110 of a donor will cause an immune reaction if transfused into the recipient. For example, if the allele profile of a donor indicated the donor's blood contained blood cell 110.3 and the allele profile of a recipient indicated the recipient's blood to contain blood cell 110.1, then since proteins 1.1 match, no immune reaction would be caused by (the antigen associated with) protein 1.1, but since the donor's blood cell 110.3 has an antigen associated with protein 2.2 (encoded by DNA-3 polymorphism 2), and the recipient's blood cell has an antigen associated with protein 2.1 (encoded by DNA-1 polymorphism 2), an immune reaction may occur in the recipient. Were cell 110.3 to lack the antigen associated with protein 2.2, then donor cells 110.3 would be acceptable for transfusion to the recipient. This example illustrates that the allele profile of DNA may be used to determine whether or not the blood of a donor may cause an immune reaction in a recipient.

EMBODIMENTS OF THE INVENTION

Figure 2:
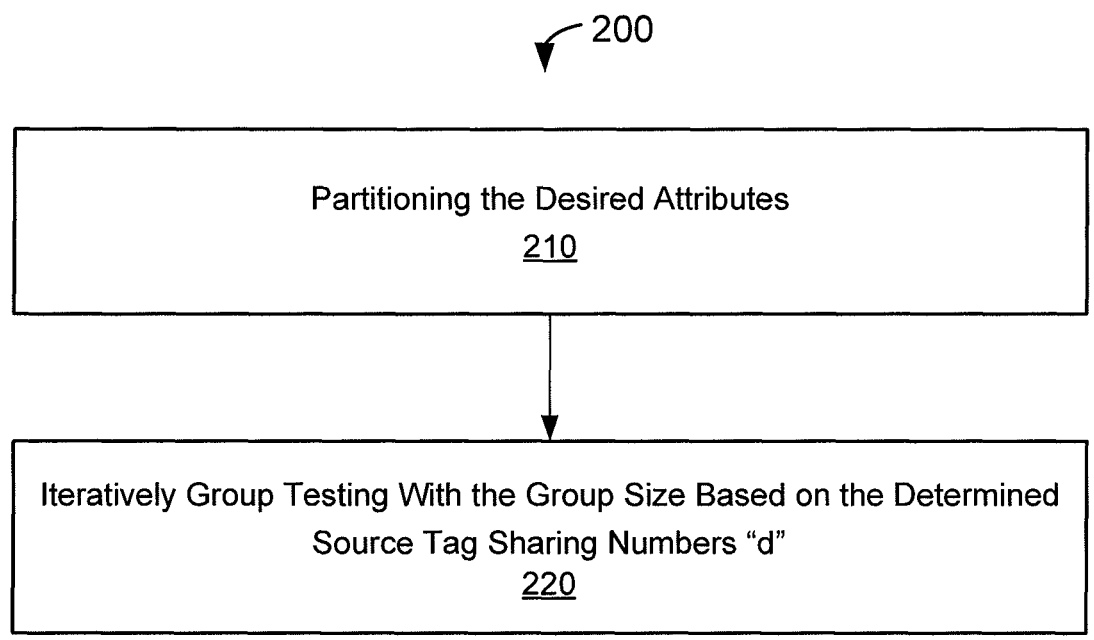
FIG. 2 schematically illustrates a method of selecting biological samples from a plurality of biological samples based on one or more desired attributes.

FIG. 2 illustrates a method of selecting biological samples from a plurality of biological samples based on one or more desired attributes. In some embodiments, the biological samples are nucleic acid samples and the one or more desired attributes are alleles. The biological samples of the plurality may be sourced from different individuals.

The attributes may have different frequencies of occurrence for each of a plurality of biological samples. For example, alleles that determine blood group antigens on a cell surface may have different frequencies. See FIGS. 8A and 8B for an explanation of the different frequencies of exemplary blood group antigens.

As depicted in FIG. 2, the method 200 comprises step 210 partitioning the desired attributes of biological samples, for instance, by determining source tag sharing numbers "d" for the desired attributes, and step 220 of group testing, optionally iteratively, the biological samples with the group size based on the determined source tag sharing numbers "d".

"Binning" means to partition two or more attributes into one or more different bins, which may be referred to as groups, categories, or subsets, based on the frequency of each of the attributes. "Group testing" refers to identifying one or more specific attributes in a common mixture comprising a plurality of biological samples. In some embodiments, the binning is provided to the method, or to the practitioner of the method, rather than the method determining the source tag sharing number "d".

Some embodiments of the method include: selecting biological samples from a plurality of biological samples based on a set of desired attributes.

Some Embodiments of Method 200 Include Selecting Nucleic Acid Samples From a Plurality of Nucleic Acid Samples Based on One or More Desired Attributes.

Figure 3A:
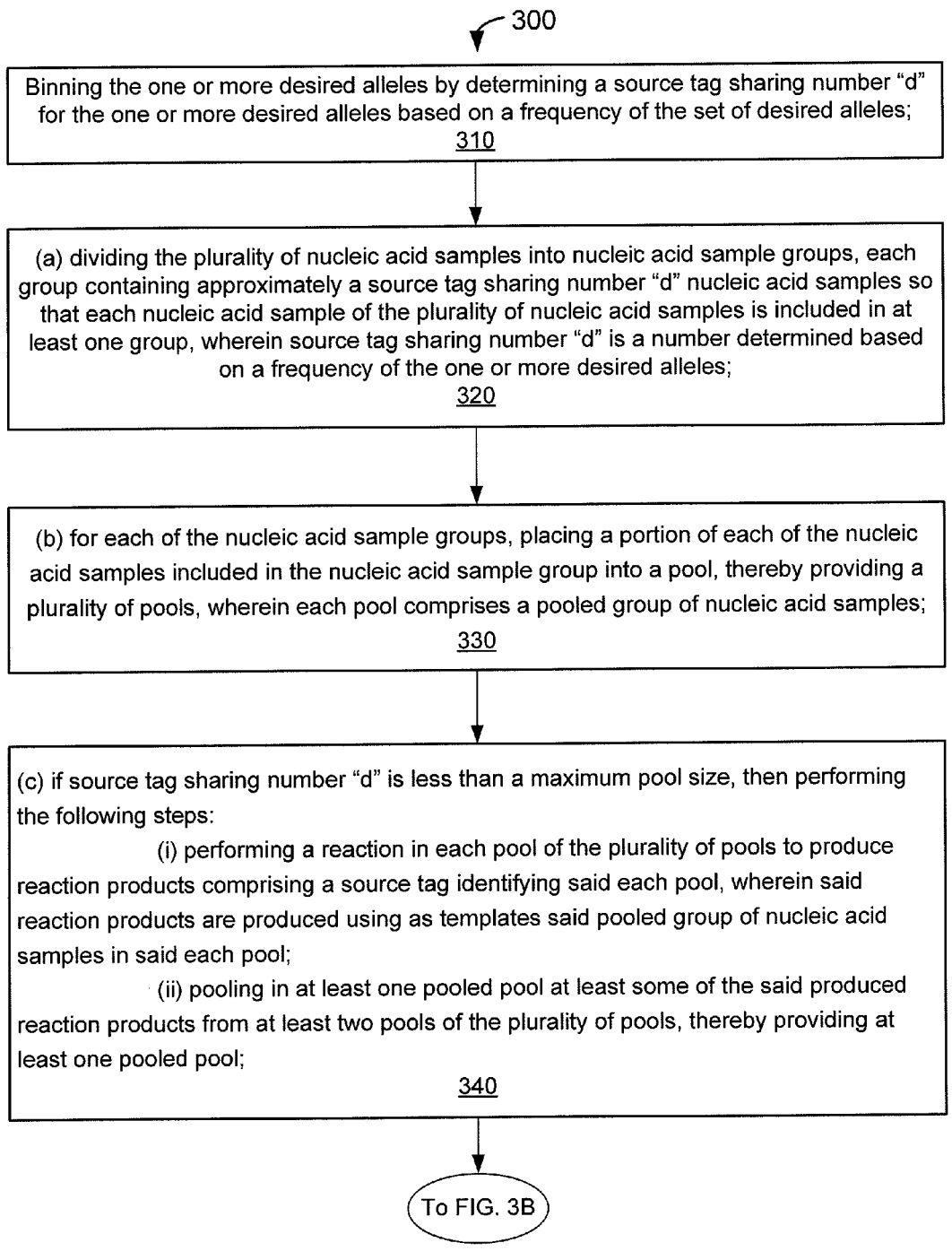

The method 300 of FIG. 3 may begin with step 310 binning attributes of the biological samples to determine source tag sharing numbers "d" for one or more desired attributes, wherein the binning is based on the frequency of the attributes.

In embodiments, the method 300 does not include step 310, but rather, the source tag sharing numbers "d" are determined prior to the performance of the method. In embodiments, the source tag sharing numbers "d" are determined for one or more desired attributes without explicitly binning the attributes. The values of source tag sharing numbers "d" will determine the number of biological samples that share the same source tag. Source tag sharing numbers "d">1 can be more efficient when the frequency of an attribute is low as explained below. Additionally, source tag sharing number of "d"=1 can be more efficient for determining attributes of biological samples as is explained below. The explanation of step 310 is provided below. For the current explanation, a source tag sharing number "d" value of "32" will be used for the "one or more desired attributes."

The source tag sharing numbers may not necessarily be determined explicitly, but implicitly by the number of nucleic acid source samples sharing source tags and/or the number of nucleic acid source samples grouped together in the steps of method 300.

Figures 4A, 4B:
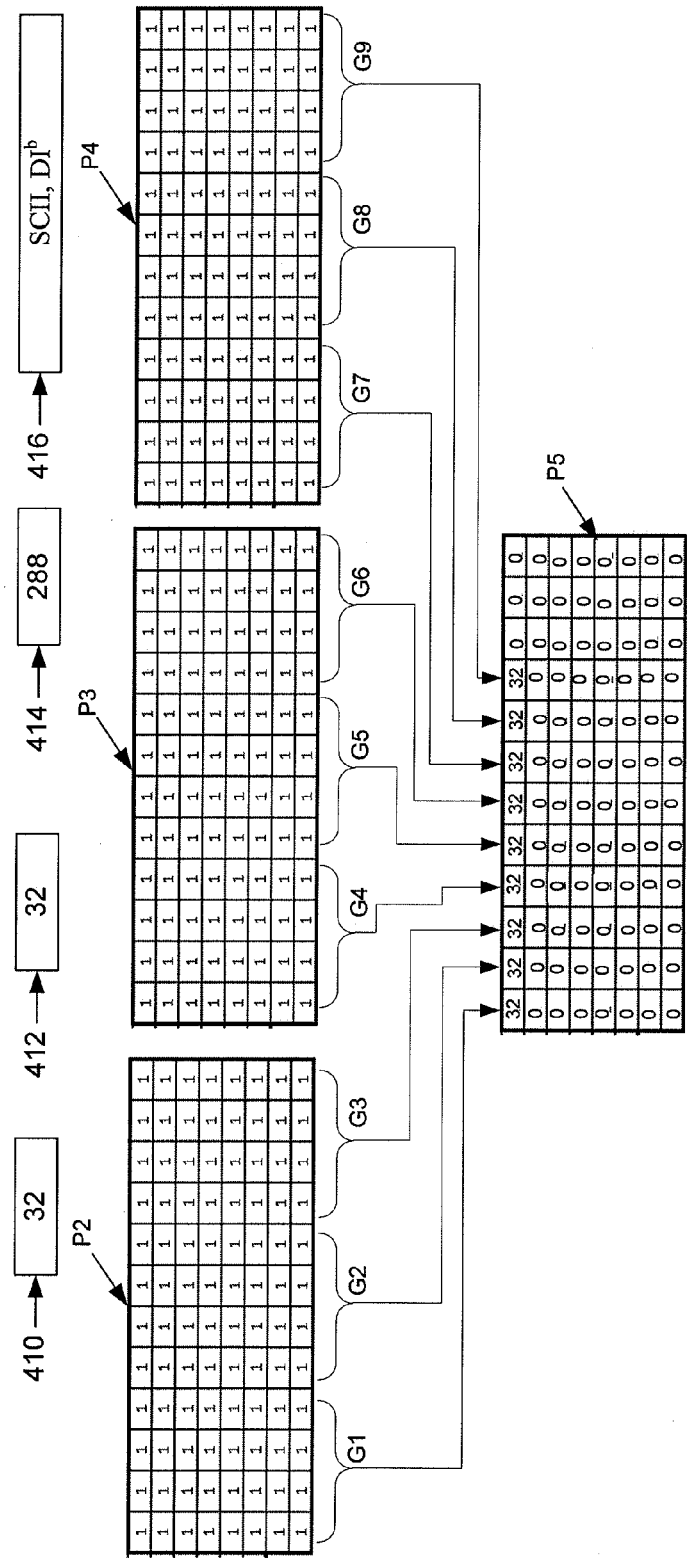
FIG. 4A schematically illustrates a numbering scheme for a plate.
FIG. 4B schematically illustrates an aspect of example of selecting biological samples from 288 biological samples based on a set of "2" desired alleles.

The method 300 of FIG. 3 will be explained in conjunction with the example illustrated in FIG. 4. Elements in FIG. 4 are identified with a "P" when the element illustrates a plate, a "G" when the element identifies a group, and a "w" when the element illustrates a well. FIG. 4A illustrates a numbering system for identifying ninety-six wells w1 . . . w96 of plate P1. So, for example w1 is well "1" of plate 1. W33 is well 33 of plate 1, w96 is well 96 of plate 1, and so forth. This numbering system for identifying wells of a plate P1 is to provide a convenient way to refer to a well of a plate P1 in the following examples. The numbers in the wells of the plates in later figures may indicate the number of biological samples in the well (such as illustrated in FIG. 4B) rather than the well number, such as illustrated in FIG. 4A. The plate P1 (or microtiter plate) is a general purpose laboratory consumable that often contains ninety-six (96) (8 rows by 12 columns) wells and may be used to perform experiments with samples that comprise nucleic acid samples.

FIG. 4B illustrates an example of selecting biological samples from 288 biological samples based on a set of "2" desired attributes. As discussed above "d" is "32" (element 412.) A maximum pool size (element 410) for the example illustrated in FIG. 4B is "32." "288" DNA samples (element 414) will be used. The following are the desired attributes, which in this example are alleles SCII and DI$^b$ (element 416), where in each case, the variant form of the allele is being used to select the DNA samples. SCII is the variant allele of the Scianna blood group system, and DI$^b$ is the variant allele of the Diego blood group system. Each of these variant alleles has a probability of being present of "0.2" percent or less.

The following describes preparing the biological samples for use in the method. A pipette is used to place a DNA sample from each of 288 aliquots of DNA samples in each of the wells of the three plates P2, P3 and P4. The "1"'s in the wells of the plates P2, P3, and P4 indicate that "1" DNA sample is in the well. The numbering of the wells described in FIG. 4A will be used to refer to the wells.

In at least one embodiment, the blood samples are pooled and then DNA is extracted from the pooled blood samples rather than first extracting the DNA and then pooling the DNA samples. In at least one embodiment, the DNA may be a different kind of nucleic acid sample.

In embodiments that do not start with step 310, the method 300 of FIG. 3 begins with step 320 (a): dividing the plurality of nucleic acid samples into nucleic acid sample groups, each group containing approximately source tag sharing number "d" nucleic acid samples so that each nucleic acid sample of the plurality of nucleic acid samples is included in at least one group.

FIG. 4B illustrates dividing "288" DNA samples (element 414) into groups G1, G2, G3, G4, G5, G6, G7, G8, G9 of "32" DNA samples each. Note that the number of DNA samples used, "288," is evenly divisible by the source tag sharing number "32." If a number of DNA samples were used that was not evenly divisible by "32", then the size of the groups may vary so that the groups are approximately "32" nucleic acid samples. Some variations in the size of the groups will not affect the outcome of the method, but may make the method less efficient. For example, suppose "291" DNA samples were used, then one group may include only "3" DNA samples, which will not affect the outcome of the method, but may make the method less efficient.

In at least one embodiment, the DNA samples may be implicitly divided into groups by the actual formation of the pools in step (b), so that step (a) need not be explicitly performed.

The method 300 of FIG. 3 continues with step 330 (b): for each of the nucleic acid sample groups, placing a portion of each of the nucleic acid samples included in the nucleic acid sample group into a pool, thereby providing a plurality of pools, wherein each pool comprises a pooled group of nucleic acid samples.

Referring to FIG. 4B, a pipette is used to place a portion of the DNA samples from wells w1 to w32 of plate P2 into well w1 of plate P5 to form a pool comprising group G1 of DNA samples. Similarly, pools comprising groups G2 through G9 of DNA samples are formed.

In some embodiments, the DNA may be gDNA extracted from nucleated cells prior to step (b). The gDNA may be extracted separately for each sample. In some embodiments, the individual samples may be pooled and the gDNA extracted from the pooled samples, when it is intended that pooled gDNA will receive source-tags comprising the same unique oligonucleotide tag. In some embodiments, the DNA is a different nucleic acid.

The method 300 of FIG. 3 continues with step 340 (c): if source tag sharing number "d" is less than is maximum pool size, then performing steps: (i) and (ii). The details of steps (c)(i) and (ii) are discussed below. In the example illustrated in FIG. 4B, the source tag sharing number "d" is "32" (element 412) and the maximum pool size is "32" (element 410), so step (c) is not performed. Step 340 (c) will be performed in an iteration of the method discussed below (with respect to FIG. 5). In some embodiments, step 340 (c) is performed even if the source tag sharing number "d" is not less than the maximum pool size.

The method 300 of FIG. 3 continues with 350 (d): if source tag sharing number "d" is less than the maximum pool size, then performing step: (d)(i). In the example of FIG. 4B, the source tag sharing number "d" is "32," which is not less than the maximum pool size, which is "32", so step (d)(i) is not performed. The details of step (d)(i) are discussed below when an iteration of the method is performed with a source tag sharing number "d" that is less than 32. The following alternative step 350 is performed: otherwise if source tag sharing number "d", which is "32," is equal to or greater than the maximum pool size, which is "32," then perform the following step 350 (d)(ii): for each of the alleles of the one or more desired alleles, performing a second reaction in each pool of the plurality of pools to produce allele-specific second reaction products comprising a marker tag. The marker tag may be used to identify an allele at a polymorphic site. Note that for convenience, in step (d)(ii), the reaction is referred to as a second reaction even though here the source tag sharing number "d" is equal the maximum pool size, so there is no first reaction. In some embodiments, step 350 (d)(i) is performed (e.g., a first reaction) even if the source tag sharing number "d" is not less than the maximum pool size.

Figure 4C:
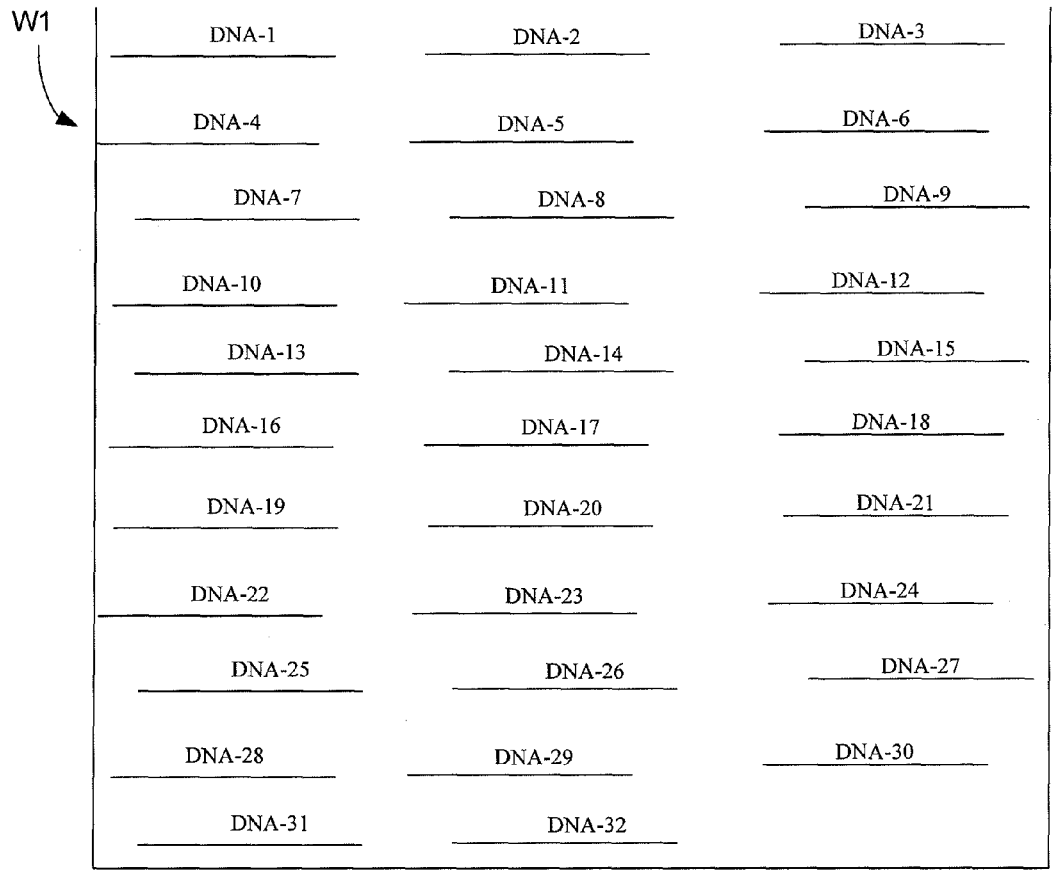
FIG. 4C schematically illustrates a well with "32" DNA samples.

FIG. 4C illustrates well "w1" of plate P5 (FIG. 4B) with "32" DNA samples, DNA-1, DNA-2, . . . , DNA-32. The DNA samples are illustrated as a single line, but the samples may include multiple, separate molecules of DNA, such as a portion of a chromosome, so that the DNA sample includes each of the polymorphic sites that are going to be interrogated in later steps.

Figure 4D:
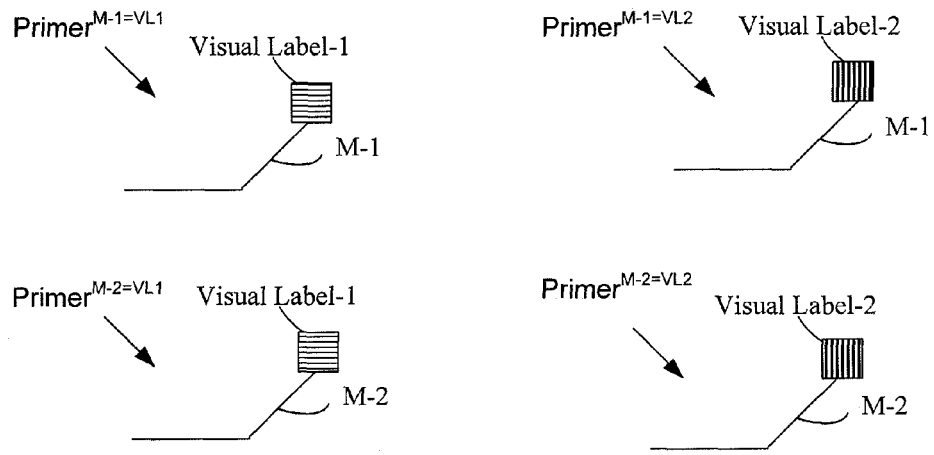
FIG. 4D schematically illustrates four allele-specific primers.

In one embodiment of step (d) (ii), allele-specific primers directed to the polymorphisms SC169 and DI2561 are added to wells w1, w9, w17, w25, w33, w41, w49, w57, and w65 (see the well numbering scheme of FIG. 4A) of plate P5. For example, FIG. 4D illustrates allele-specific primers, $primer^{M-1=VL1}$, $primer^{M-1=VL2}$, $primer^{M-2=VL1}$, $primer^{M-2=VL2}$. $Primer^{M-1=VL1}$ is an allele-specific primer for SCI, $primer^{M-1=VL2}$ is an allele-specific primer for SCII, $Primer^{M-2=VL1}$ is an allele-specific primer for $DI^a$, and $primer^{M-2=VL2}$ is an allele-specific primer for $DI^a$. The primers include either M-1 or M-2, which are unique oligonucleotide tags, and either VL1 or VL2, which are visual labels. The combination of a unique oligonucleotide tag with a visual label is the marker tag in this case and provides enough information to identify the allele.

The samples in wells w1, w9, w17, w25, w33, w41, w49, w57, and w65 are then amplified, for example using PCR with the DNA samples in the wells being used as a template, so that if a DNA sample contains an allele, then an amplicon is produced with a marker tag identifying the allele.

Figure 4E:
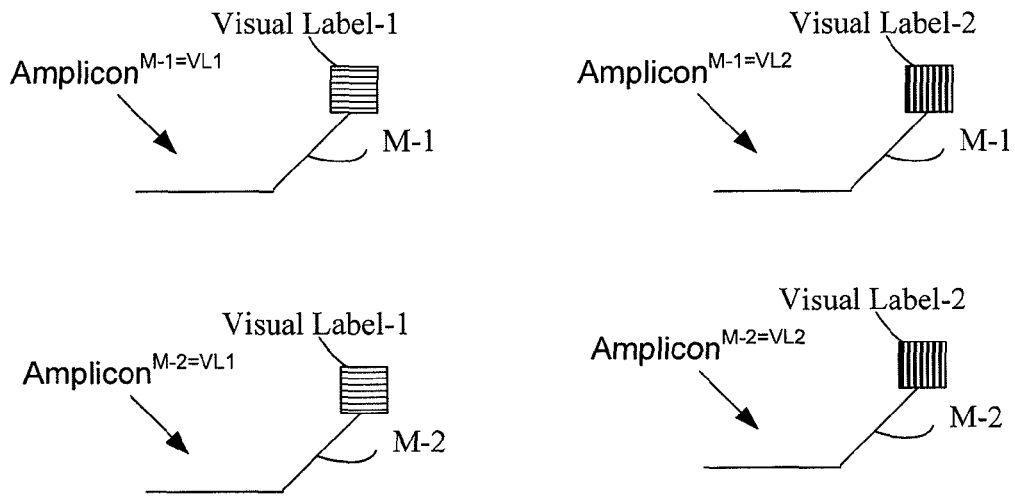
FIG. 4E schematically illustrates four types of amplicons that could be produced using the four allele-specific primers depicted in FIG. 4D.

For example, FIG. 4E illustrates the four types of amplicons that could be produced as a result of the amplification. $Amplicon^{M-1=VL1}$ would be produced from $primer^{M-1=VL1}$ and a DNA sample with allele SCI, $amplicon^{M-1=VL2}$ would be produced from $primer^{M-1=VL2}$ and a DNA sample with allele SCII, $amplicon^{M-2=VL1}$ would be produced from $primer^{M-2=VL1}$ and a DNA sample with allele $DI^a$, and $amplicon^{M-2=VL2}$ would be produced from $primer^{M-2=VL2}$ and a DNA sample with allele $DI^b$. Notice that because step 340 (c) was not performed in this iteration, the amplicons cannot be distinguished based on which DNA sample was used as a template to produce the amplicon, which is a characteristic of "group testing," and note that SCII and $DI^a$ are binned together in that the alleles are being tested together.

As a further example, if DNA-13 in well w1 of plate P5 contained allele SCII, that is allele "II" of polymorphism SC169, then $primer^{M-1=VL2}$ would anneal to the allele "II" of the DNA-13 sample, and be amplified to produce $amplicon^{M-1=VL2}$. Again, there is no distinction between the amplicons produced from the different DNA samples.

The method 300 of FIG. 3 continues with step 360 (e): if source tag sharing number "d" is less than the maximum pool size, then performing step (e)(i). In the example of FIG. 4B, the source tag sharing number "d" is 32, which is not less than the maximum pool size, which is "32", so step (e) (i) is not performed. The details of step (e) (i) are discussed below when an iteration of the method is performed with a source tag sharing number "d" that is less than "32." The following alternative step 360 is performed: otherwise if source tag sharing number "d" is equal to or greater than the maximum pool size, then perform the following step (e) (ii): identifying said allele-specific second reaction products by interrogating said marker tag to identify which pools of the plurality of pools includes at least one nucleic acid sample that has an allele of the one or more desired alleles, thereby identifying which of the plurality of groups of nucleic acid samples includes a nucleic acid sample with at least one allele of the one or more desired alleles. In some embodiments, step (e)(i) is performed even if the source tag sharing number "d" is not less than the maximum pool size.

Figure 4F:
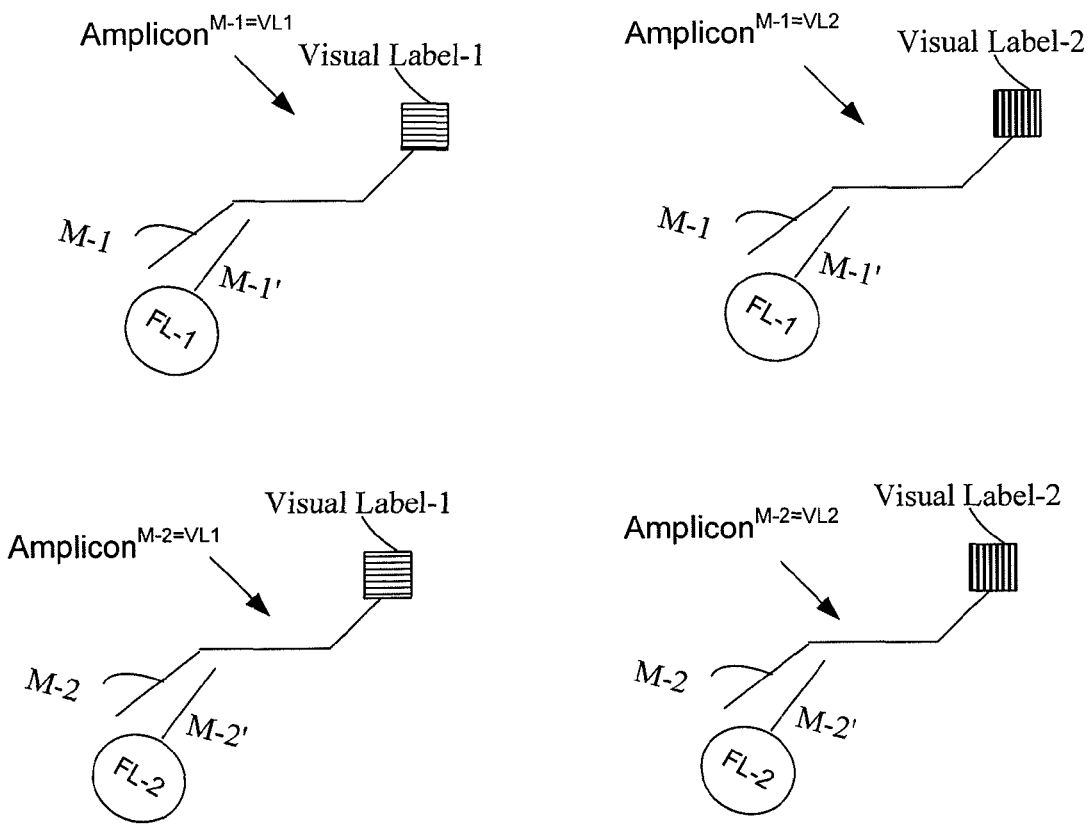
FIG. 4F schematically illustrates an embodiment of identifying allele specific second reaction products using microparticles comprising a fluorescent label.

FIG. 4F illustrates how some embodiments identify allele specific second reaction products. The alleles are identified, using microparticles 1 and 2; microparticles are also referred to as "beads" or "microbeads", and are typically 1 um or several um in diameter. Microparticles 1 and 2 are added to the wells w1, w9, w17, w25, w33, w41, w49, w57, and w65. The microparticles comprise attached oligonucleotides probes M-1' or M-2', hereinafter referred to as "capture probes." A capture probe comprises at least one nucleotide sequence that is complementary to a target nucleic acid. Here capture probe M-1' comprises a nucleotide sequence complementary to the nucleic acid sequence of unique oligonucleotide tag M-1. Similarly, capture probe M-2' comprises a nucleotide sequence complementary to the nucleic acid sequence of unique oligonucleotide tag M-2. The microparticles also comprise a fluorescent label, or mixture of such labels differing in color, that identifies the microparticles and thus the capture probes attached to the microparticle. The fluorescent label may comprise an encoded fluorescence such as described in U.S. Pat. No. 7,498,054, entitled "METHOD FOR CONTROLLING SOLUTE LOADING OF POLYMER MICROPARTICLES", the entire disclosure of which is incorporated herein by reference or U.S. Pat. No. 7,083,914, entitled "Color-Encoding AND IN-SITU INTERROGATION OF MATRIX-COUPLED CHEMICAL COMPOUNDS", the entire disclosure of which is incorporated herein by reference.

The second reaction products may be identified because they anneal to complementary capture probes on the microparticles 1, 2, and the marker tags on the second reaction products also comprise fluorescent labels which can be used to determine which allele is at the polymorphic site.

For example, illustrated in FIG. 4F are "4" microparticles, two with a fluorescent label of "FL-1" for the polymorphic site SC169, and two with a fluorescent label of "FL-2" for polymorphic site DI2561. Amplicon$^{M-1=VL1}$ and amplicon$^{M-1=VL2}$ would anneal to the microparticles with capture probe "M-1". Amplicon$^{M-2=VL1}$ and amplicon$^{M-2=VL2}$ would anneal to the microparticles with capture probe "M-2".

The microparticle fluorescent tag is then used to identify the polymorphic site (FL-1 is SCI169 and FL-2 is DI2561), and the fluorescent tag on the allele-specific second reaction products can be used to identify the allele (visual-label-1 identifies SCI for FL-1, and visual-label-1 identifies $DI^a$ for FL-2). The following explains microparticle-mediated allele identification in more detail.

For the example illustrated in FIG. 4, visual label "VL1" is detected near fluorescent labels "FL-1" and "FL-2" in all of the groups G1, ..., G9 (FIG. 4B.) This result identifies that all of the groups G1 ... G9 include one or more DNA samples that have alleles SCI and $DI^a$, but does not identify which of the DNA samples specifically have alleles SCI and $DI^a$. Only if no visual label V2 is detected in a group can the alleles for all the samples in the group be unambiguously identified.

Visual label "VL2" is detected near fluorescent label "FL-1" only in groups G1 (w1), G4 (w25), and G8 (w57). See FIG. 4B which matches wells to groups. This result indicates that groups G1, G4, and G8 include one or more DNA samples that have alleles SCII, thereby identifying which of the plurality of groups of nucleic acid samples includes a nucleic acid sample with at least at least one desired allele. But this result does not identify which of the DNA samples specifically have allele SCII. Visual label "VL2" is detected near fluorescent label "FL-2" only in groups G1 and G8. This result indicates that groups G1 and G8 include one or more DNA samples that have allele $DI^b$, thereby identifying which of the plurality of groups of nucleic acid samples includes a nucleic acid sample with at least at least one desired allele. But again, this result does not identify which of the DNA samples specifically have $DI^b$.

Accordingly, groups G1, G4, and G8 would be selected as including at least one of the desired alleles, SCII and $DI^b$.

In at least one embodiment, rather than testing for both the desired allele and the alternative allele at a bi-allelic polymorphic site, only the desired allele may be tested for, in order to identify which of the plurality of groups of nucleic acid samples includes a nucleic acid sample with at least at least one desired allele. For example, in the example of FIG. 4 only the primers primer$^{M-1=VL2}$ and primer$^{M-2=VL2}$ would be added to the wells to determine which of the groups include one or more desired alleles SCII and $DI^b$.

The method 300 continues with step 370 (f): if there are one or more additional desired alleles, then selecting the nucleic acid samples of the identified groups from the plurality of nucleic acid samples, and repeating steps (a)-(e) with the selected nucleic acid samples as the plurality of nucleic acid samples, and the additional desired alleles as the one or more desired alleles, otherwise selecting the nucleic acid samples of the identified groups from the plurality of nucleic acid samples.

In the example of FIG. 4, the identified groups are G1, G4, and G8, because G1, G4, and G8 have been identified as having at least one DNA sample that has allele SCII, and G1 and G8 have been identified as having at least one DNA sample that has $DI^b$. The selected DNA samples are then the DNA samples of G1, G4, and G8, which are DNA samples 1-32, 97-128, and 225-256, respectively.

The steps (a)-(e) are repeated if there are additional desired alleles. In the iteration, the selected nucleic acid samples are the plurality of nucleic acid samples, and the additional desired alleles are the one or more desired alleles. The additional desired alleles may be other alleles that are not part of the one or more alleles. The additional desired alleles may be alleles that have a higher frequency than the one or more desired alleles.

FIG. 5 illustrates the steps (a)-(e) being repeated with the plurality of nucleic acid samples being the selected DNA samples 1-32, 97-128, and 225-256, which is "96" DNA samples of the initial "288" DNA samples, and the one or more desired alleles being additional desired alleles of the variant of K(1/2) (Kell blood group system) and the variant of FY265 (Duffy blood group system). A lower value of source tag sharing number "d" source of "d"="16" is used.

As discussed above "d" is "16" (element 512.) A maximum pool size (element 510) continues to be "32". "96" DNA samples (element 514) will be used. K(1/2) and FY265 will be the one or more desired alleles (element 516). In each case, the variant form of the allele is being used to select the DNA samples. Each of the alleles has a probability of being present of "1" percent or less. Optionally, at least one of the desired alleles, SCII and $DI^b$. may be tested for again, while testing for desired alleles K(1/2) and FY265 in steps (a)-(e) of FIG. 5.

Repeating steps (a)-(e) of method 300 of FIG. 3 begins with step 320 (a): dividing the plurality of nucleic acid samples into nucleic acid sample groups, each group containing approximately source tag sharing number "d" nucleic acid samples so that each nucleic acid sample of the plurality of nucleic acid samples is included in at least one group.

Figure 5A:
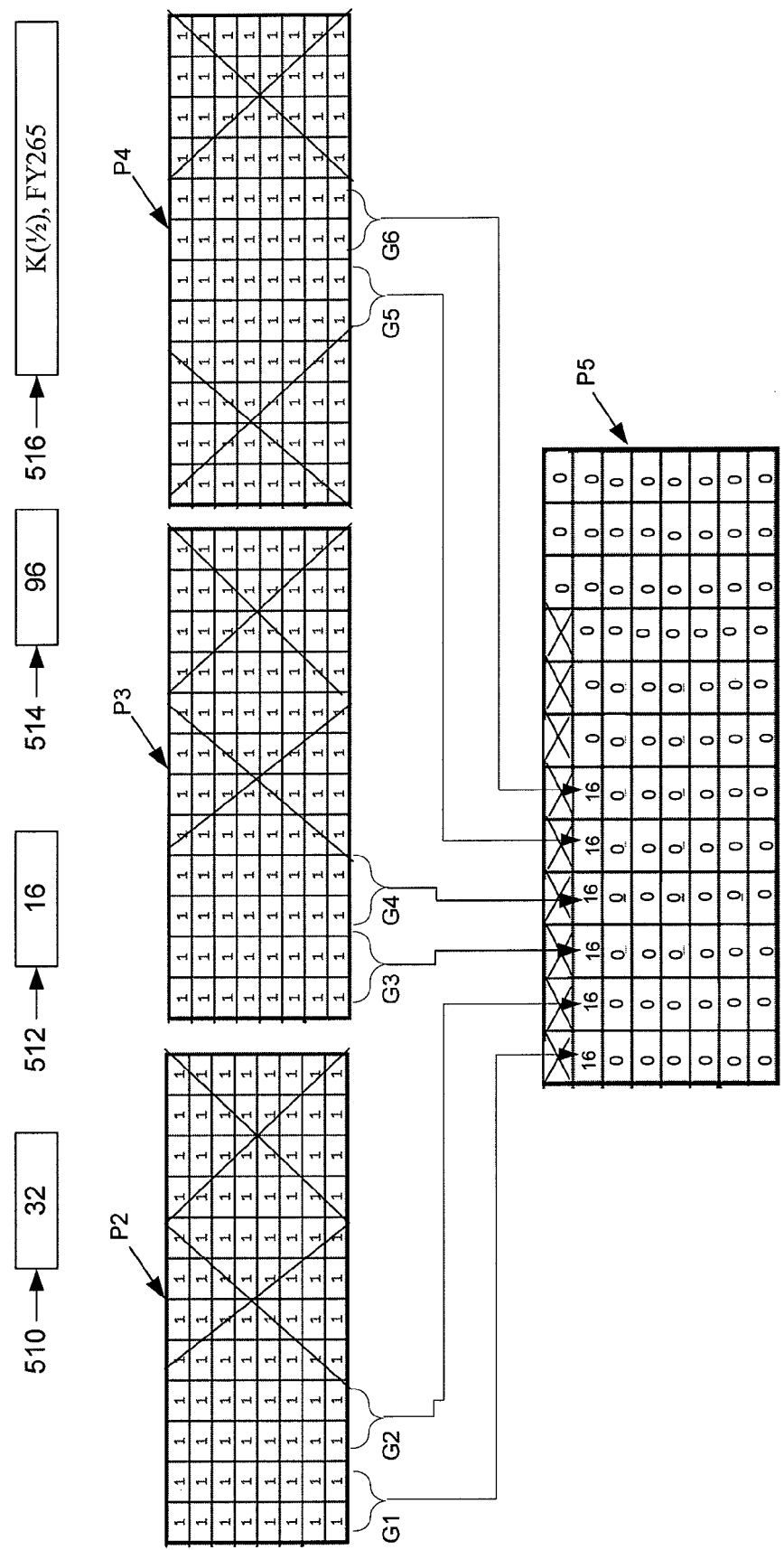
FIGS. 5A-5H schematically illustrates the steps (a)-(e) being repeated for source tag sharing number "d"="16"

FIG. 5A illustrates dividing "96" DNA samples (element 514) into groups G1, G2, G3, G4, G5, G6 of "16" DNA samples each. The remaining 192 samples, which are crossed out in plates P2, P3 and P4 in FIG. 5A, may be eliminated from further consideration, since they do not comprise one or more desired alleles SCII and $DI^b$. The maximum pool size (element 510) is still "32". Allele K(1/2) and FY265 (element 516) are still the desired attributes. Also, the names G1, G2, G3, G4, G5, and G6 are being re-used to represent different groups of the DNA samples.

The method 300 of FIG. 3 continues with step 330 (b): for each of the nucleic acid sample groups, placing a portion of each of the nucleic acid samples included in the nucleic acid sample group into a pool, thereby providing a plurality of pools, where each pool comprises a pooled group of nucleic acid samples.

Referring to FIG. 5A, a pipette is used to place a portion of the DNA samples from wells w1 to w16 of plate P2 (refer to FIG. 4A for well numbering) into well w2 of plate P5 to form a pool comprising group G1 of DNA samples. Similarly, pools comprising G2 through G6 DNA samples are formed in wells w10, w18, w26, w34, and w42, respectively, of P5. Note that many other ways are possible to get the group of DNA samples pooled into a well or other functionally equivalent container. The described embodiment is meant to be illustrative (and not limiting) of one method of forming the pools. Note that wells of P5 were used, but that another plate could have been used.

The method 300 of FIG. 3 continues with step 340 (c): if source tag sharing number "d" is less than a maximum pool size, then performing the following steps: (i) performing a reaction in each pool of the plurality of pools to produce reaction products comprising a source tag identifying said each pool, where said reaction products are produced using as templates said pooled group of nucleic acid samples in said each pool. And, step (ii) of pooling in at least one pooled pool at least some of the said produced reaction products from at least two pools of the plurality of pools, thereby providing at least one pooled pool. In the example illustrated in FIG. 5, the source tag sharing number "d" is "16" (element 512) and the maximum pool size is "32" (element 510), so step 340 (c) is performed.

In one or more embodiments, step 340 (c)(i) comprises for each pool of the plurality of pools amplifying the nucleic acid samples in the pool with primers comprising a source tag to produce amplicons comprising said source tag identifying said each pool, where said amplicons are produced using as templates said pooled group of nucleic acid samples in said each pool.

Amplification may be performed by conventional methods of nucleic acid amplification, e.g., polymerase chain reaction (PCR).

Figure 5B:
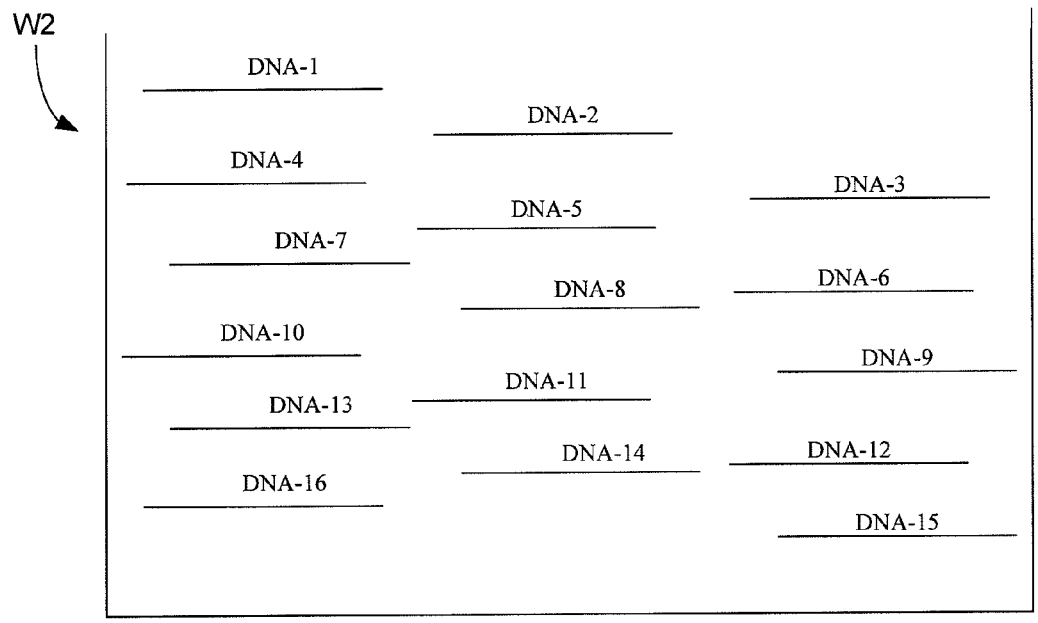
Figure 5C:
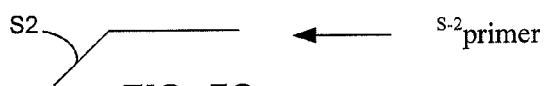

The amplification is now described in greater detail. FIG. 5B illustrates well "w2" with DNA samples "1" through "16" pooled together prior to step (c)(i). FIG. 5C illustrates a primer with source-tag s2 identifying the pool present in well "w2". Primers with source-tag s2, which may be represented as $^{s-2}$primer, are placed in well "2" and primers with source-tags identifying the other wells, $^{s-10}$primer, $^{s-18}$primer, $^{s-26}$primer, $^{s-34}$primer, and $^{s-42}$primer, are placed in the other wells w10, w18, w26, w34, and w42 of plate P5. In some embodiments, the source tags comprise so-called oligonucleotide "barcodes". The sequence for the source tags may be selected from a set of unique non-naturally occurring coding sequences, which may be referred to as "barcodes." The barcodes may be replicated in a later step along with the sequence of nucleotides of the DNA. See, "Address/capture tags for flow-cytometry based mini-sequencing", "Kind Code A1", White, et al. (U.S. Pat. Pub. 20050147998, Jul. 7, 2005), the entire disclosure of which is incorporated herein by reference; and see, "Oligonucleotide tags for sorting and identification", Brenner, et al. (U.S. Pat. No. 6,352,828, 2004), the entire disclosure of which is incorporated herein by reference. In one or more embodiments, the source tag may identify the pool according to length of the source tag as is described below with electrophoresis.

If the DNA samples have different DNA molecules for the desired alleles, such as a molecule containing the portion of the chromosome sequence comprising the variant of K(1/2), and another molecule containing the portion of the chromosome sequence comprising the variant of FY265, then the $^{s-2}$primer would actually need to be more than one primer to amplify both molecules of the DNA. So, although illustrated as a single primer each of the primers may include a primer for each of the selected sections of the DNA molecule needed to determine the polymorphism. Note too that although referred to as DNA, the sample may be any nucleic acid samples.

Figure 5D:
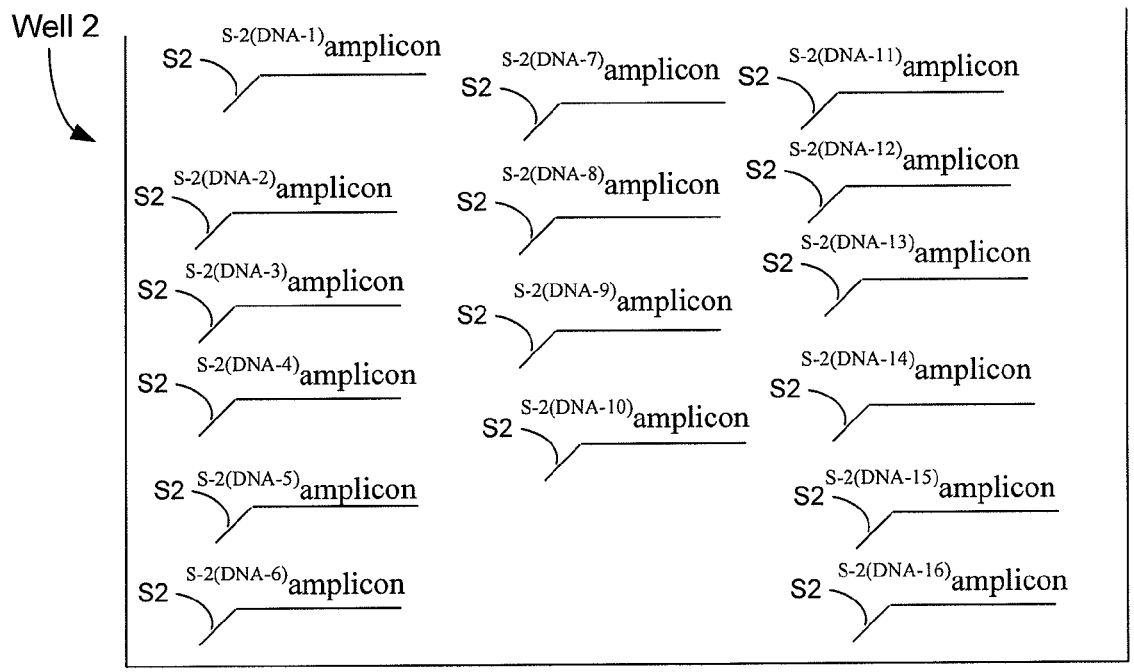

Nucleic acid samples, here DNA of the pools in wells w2, w10, w18, w26, w34, and w42, are then amplified to produce respectively $^{s-2}$amplicon, $^{s-10}$amplicon, $^{s-18}$amplicon, $^{s-26}$amplicon, $^{s-34}$amplicon, and $^{s-42}$amplicon. The notation $^{s-2}$amplicon denotes amplicons from the different DNA samples in well w2. FIG. 5D illustrates well "w2" after amplification. The notation $^{S-2(DNA-1)}$amplicon denotes an amplicon elongated using DNA-1 as a template and with a source tag s-2 attached. Amplification may comprise, for example, PCR. In general, different methods may be used to produce amplicons, $^{S-2}$amplicon, $^{S-10}$amplicon, $^{S-18}$amplicon, $^{s-26}$amplicon, $^{s-34}$amplicon, and $^{s-42}$amplicon, from the different DNA samples.

In some embodiments, any number of PCR cycles may be used for amplification generation. In some embodiments, a small number of cycles (8-10 or fewer cycles) of PCR may be used. The source tags may be replicated in a later step along with a sequence of nucleotides of the template DNA containing the polymorphic site. The notation $^{S-2(DNA-1)}$ amplicon may represent different amplicons produced from more than one primer. As discussed above, PCR may not replicate the entire DNA template, but can be used to replicate only the portion of the DNA template that includes the polymorphic sites being interrogated. In general, a primer may only replicate the portion of the DNA needed to identify a single polymorphism, so different primers may need to be used for each polymorphism.

As discussed above, more than one primer may be used, because the desired alleles may be on different molecules of the DNA.

Step 340 (c) of method 300 in FIG. 3 continues with (ii): pooling in at least one pooled pool at least some of the said produced reaction products from at least two pools of the plurality of pools, thereby providing at least one pooled pool.

Figure 5E:
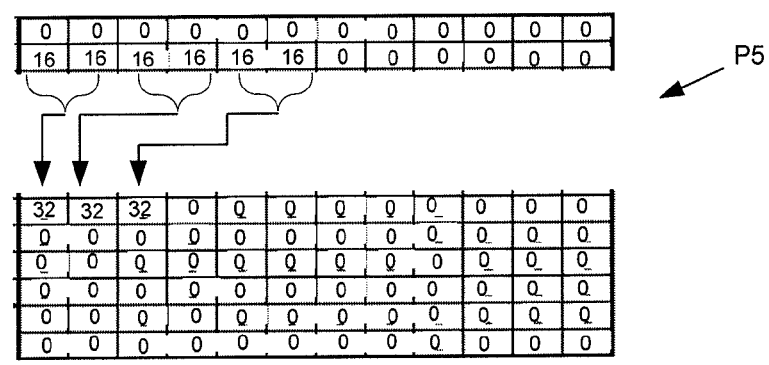

Continuing with the example of FIG. 5, as illustrated in FIG. 5E, a pipette is used to pool together wells "w2" (G1) and "w10" (G2) into well "w3" (see FIG. 4A for well numbering), to pool together wells "w18" (G3) and "w26" (G4) into well "w11", and to pool together wells "w34" (G5) and "w42" (G6) into well "w19." After the pooling, well "w3" comprises $^{S-2}$amplicons and $^{S-10}$amplicons, well "w11" comprises $^{S-18}$amplicons and $^{S-26}$amplicons, and well "w19" comprises $^{S-34}$amplicons and $^{S-42}$amplicons.

The method 300 of FIG. 3 continues with 350 (d): if source tag sharing number "d" is less than the maximum pool size, then performing step: (d)(i). In the example of FIG. 5, the source tag sharing number "d" is "16," which is less than the maximum pool size, which is "32", so step (d)(i) is performed. Step 350 (d)(i) recites: (i) for each of the one or more desired alleles, performing a second reaction in the at least one pooled pool using said reaction products comprising said source tag to produce allele-specific second reaction products comprising a marker tag and a derived source tag, where said derived source tag is at least one of: said source tag, a copy of said source tag, or a copy of the complement of the source tag, and wherein said marker tag identifies an allele at a polymorphic site, and where said second reaction is in a pooled pool of said at least one pooled pool.

In at least one embodiment of step (d) (i), allele-specific primers directed to the polymorphisms K(1/2) and FY265 are added to wells w3, w11, and w19 (see the well numbering scheme of FIG. 4A) of plate P5. In a similar manner as described above with reference to allele-specific primers used above in performing step (d)(ii), allele-specific primers are used to perform (d)(i) except the allele-specific primers are for K(1/2) and FY265. For example, FIG. 4D illustrates allele-specific primers, primer$^{M-1=VL1}$, primer$^{M-1=VL2}$, primer$^{M-2=VL1}$, primer$^{M-2=VL2}$. For step (d)(i), primer$^{M-1=VL1}$ is an allele-specific primer for the normal of K(1/2), primer$^{M-1=VL2}$ is an allele-specific primer for the variant of K(1/2), rimerM$^{-2=VL1}$ is an allele-specific primer for the normal of FY265, and primer$^{M-2=VL2}$ is an allele-specific primer for the variant of FY265. The primers include either M-1 or M-2, which are unique oligonucleotide tags, and either VL1 or VL2, which are visual labels. The combination of a unique oligonucleotide tag with a visual label is the marker tag, which provides enough information to identify the allele.

Note that K(1/2) and FY265 are binned together in that they are being group tested together.

The samples in wells w3, w11 and w19 are then amplified by, for example, using PCR with the DNA samples in the wells being used as a template, so that if a DNA sample contains an allele, then an amplicon is produced with a marker tag identifying the allele.

Figure 5F:
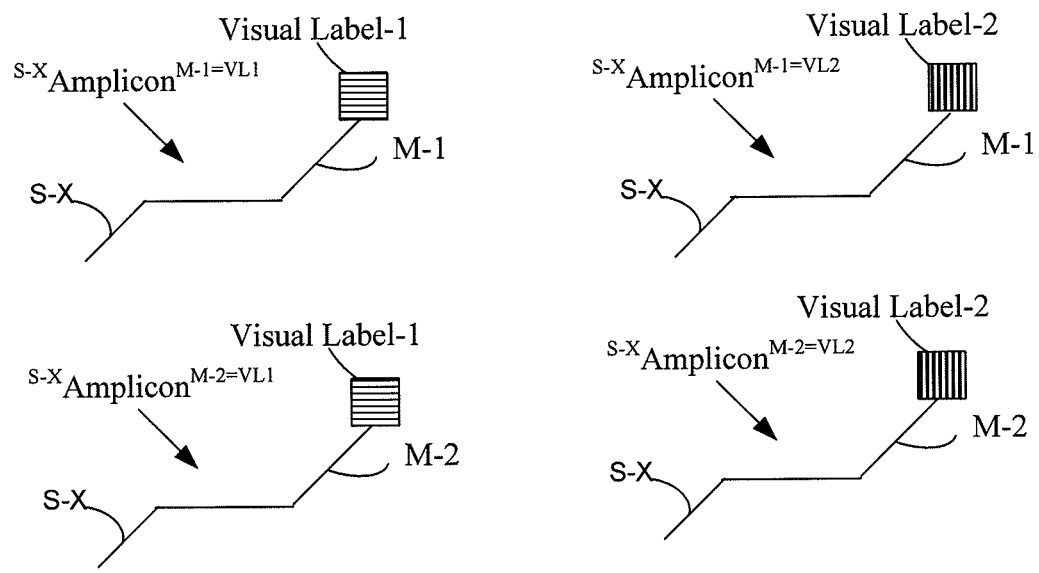

For example, FIG. 5F illustrates the four types of amplicons that could be produced as a result of the amplification in each of the wells "w3", "w9", and "w19." The four types of amplicons that could be produced as a result of the amplification are $^{S-X}$Amplicon$^{M-1=VL1}$, $^{S-X}$Amplicon$^{M-1=VL2}$, $^{S-X}$Amplicon$^{M-2=VL1}$, and $^{S-X}$Amplicon$^{M-2=VL2}$. The notation "S-X" means that "X" may be any of the numbers for the source tags that are present in the well. For example, in well "w3", $^{S-2}$Amplicon$^{M-1=VL1}$ would be produced from primer$^{M-1=VL1}$ and $^{S-2}$amplicon, if $^{S-2}$amplicon was produced from a DNA sample with the normal allele of K(1/2). Note that the source tag or complement of the source tag of the source-tagged amplicons is copied since the source tag in this embodiment is a unique oligonucleotide tag. So, in well "w3", "X" may be "2" or "10"; in well "w11", "X" may be "18" or "26"; and, in well "w19", "X" may be "34" or "42." Similarly, $^{S-X}$Amplicon$^{M-1=VL2}$ would be produced from primer$^{M-1=VL2}$ and an $^{S-X}$amplicon produced from a DNA sample with the variant allele of K(1/2); $^{S-X}$amplicon$^{M-2=VL1}$ would be produced from primer$^{M-2=VL1}$ and an $^{S-X}$amplicon produced from a DNA sample with the normal allele of FY265; and, $^{S-X}$amplicon $^{M-2=VL2}$ would be produced from primer$^{M-2=VL2}$ and an $^{S-X}$amplicon produced from a DNA sample with the variant allele FY265. Notice that the amplicons cannot be distinguished based on which DNA sample was used as a template to produce the amplicon, but that the source tags identify which of the six wells "w2", "w10", "w18", "w26", "w34", or "w42," and therefore which pool the DNA sample came from. This is a characteristic of group testing, and the fact that the variants of FY265 and K(1/2) are interrogated together in the same well indicate that the variants FY265 and K(1/2) are binned together.

The method 300 of FIG. 3 continues with step 360 (e): if source tag sharing number "d" is less than the maximum pool size, then performing step (e)(i). In the example of FIG. 4B, since the source tag sharing number "d" is "16", which is less than the maximum pool size, which is "32", step (e) (i) is performed. Step 360 (e) (i) teaches identifying said allele-specific second reaction products by interrogating said derived source tag and said marker tag to identify which pooled pools of the at least one pooled pool include at least one nucleic acid sample that has an allele of the one or more of desired alleles, thereby identifying which of the plurality of groups of nucleic acid samples includes a nucleic acid sample with at least one allele of the one or more desired alleles.

Figure 5G:
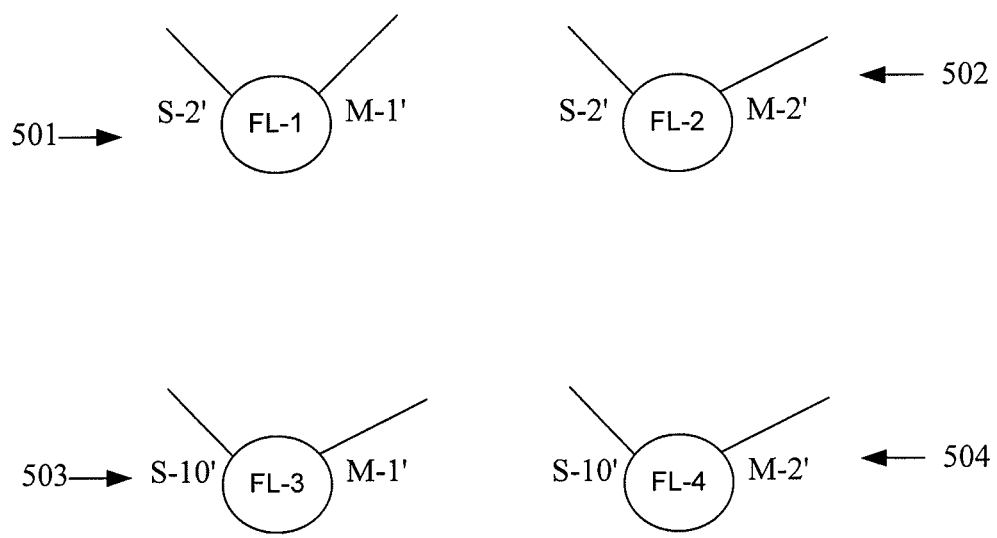

FIG. 5G illustrates how some embodiments identify allele specific second reaction products for well "w3" which contains "16" DNA samples from each of wells "w2" and "w10". Four types of microparticles 501, 502, 503, 504, are added to well "w3". The microparticles comprise capture probes M-1' or M-2' and S2' or S10'. The microparticles also comprise a fluorescent label "F-1", "F-2", "F-3", "F-4," respectively, that identifies the microparticle.

The second reaction products may be identified because they anneal to complementary capture probes on the microparticles 501, 502, 503, 504, and the marker tags on the second reaction products comprise fluorescent labels which can be used to determine which allele is at the polymorphic site.

Figure 5H:
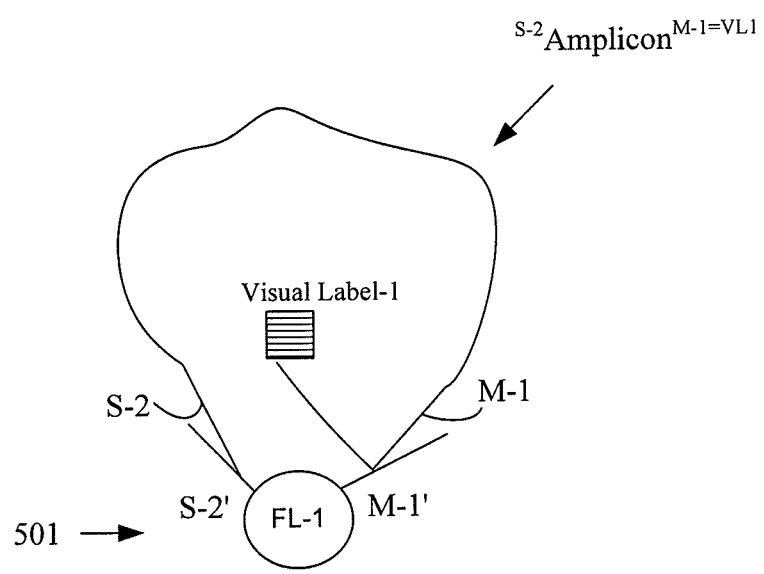

For example, illustrated in FIG. 5H is microparticle 501 with amplicon $^{S-2}$amplicon$^{M-1=VL1}$ annealed to the microparticle. The combination of $^{S-2}$amplicon$^{M-1=VL1}$ and "FL-1" indicates that at least one s-2 source tagged amplicon has the normal allele of K(1/2). Similarly, the combination of $^{S-2}$amplicon$^{M-1=VL2}$ with FL-1 indicates that at least one s-2 source tagged amplicon has the variant allele K(1/2). Similarly, for s-10 source tagged amplicons microparticle 503 is sufficient to identify whether any s-10 source tagged amplicons have the normal or variant allele of K(1/2). Similarly, microparticle 502 can be used to identify whether any s-2 source tagged amplicons have the normal or variant allele of FY265 (FL-2 and VL-1 means normal allele and FL-2 and VL-2 means variant allele). Similarly, microparticle 504 can be used to identify whether s-10 source tagged amplicons have the normal or variant allele of FY265. As discussed above, in at least one embodiment, only the desired alleles are identified. Note that if both alleles at a polymorphic site are identified then the result of the identification is ambiguous. If only one allele at a polymorphic site is identified then all of the DNA samples have the identified allele and no further testing for that allele for those DNA samples is necessary.

Thus, which of the groups include at least one DNA sample with at least one desired allele can be identified.

For the example illustrated in FIG. 5, visual labels "VL2" are detected near fluorescent labels "FL-1" in well "3", which indicate that G1 (from well "w2") includes at least one DNA with the desired allele variant of K(1/2). And, visual labels "VL2" are detected near fluorescent labels "FL-3" in well "11", which indicate that G4 (from well "w26") includes at least one DNA with the desired allele variant of K(1/2). And, visual labels "VL2" are detected near fluorescent labels "FL-1" in well "w19", which indicate that G5 (from well "w34") includes at least one DNA with the desired allele variant of K(1/2). So, G2 (well "w2"), G4 (well "w26"), and G5 (well "w34"), each have at least one DNA sample with the allele variant of K(1/2).

Furthermore, visual labels "VL2" are detected near fluorescent labels "FL-4" in well "3", which indicate that G2 (from well "w10") includes at least one DNA with the desired allele variant of FY265. And, visual labels "VL2" are detected near fluorescent labels "FL-2" in well "w19", which indicate that G5 (from well "w34") includes at least one DNA with the desired allele variant of FY265. And, visual labels "VL2" are detected near fluorescent labels "FL-1" in well "w19", which indicate that G5 (from well "w34") includes at least one DNA with the desired allele variant of K(1/2).

Accordingly, with reference to FIG. 5A, groups G1 (DNA samples, P2, w1 through w16) G2 (DNA samples, P2, w17 through w32), G4 (DNA samples, P3, w17 through w32), and G5 (P4, w33 through w48) would be selected as including at least one of the desired alleles variants of K(1/2) and FY265. Group G5 indicates that both variant of K(1/2) and variant of FY265 are present, but it is not known whether at least one DNA sample has both variant of K(1/2) and variant of FY265, or whether one or more DNA samples has variant of K(1/2) and different DNA samples have variant of FY265. Notice that the method began with "288" DNA samples and after the first iteration of the method there were only "96" DNA samples remaining, and after steps (a)-(e) were repeated once there were "64" DNA samples remaining. If steps (a)-(e) were repeated with "d"=1, then only DNA samples would remain that actually had at least one of the desired alleles.

In some embodiments, molecular beacons designed to detect designated source tag and marker tag combinations on amplicons may be used. The beacons may be color-coded to distinguish individual species beacon.

In some embodiments, capture probes complementary to source tags and/or marker tags are provided on separate spectrally distinguishable nanoparticles so that two nanoparticles will attach to the produced amplicons containing the target source tag and maker tag. Because of the specific combination of source tag and marker tag, there will be a specific dual-color signature that may be used to identify the source code and marker tag (see manufacturing instructions for use of Qdot™ Nanocrystals, Invitrogen, Carlsbad, Calif.).

See co-pending applications "Method for Determining an Allele Profile of Nucleic Acid" and "Method for Determining an Attribute Profile of Biological Samples" that illustrates microparticle designs that may be used to identify the amplicons. The allele-specific amplification or hybridization product comprising an marker tag and/or source tag anneal to the complementary capture probes on the microparticles which enables identifying those products.

In some embodiments, as discussed above, the Visual Label-1 may be omitted. In such cases, the marker tag M-1 may include a unique oligonucleotide tag that encodes for the presence of both the allele and the polymorphism site. In some embodiments, the length of the marker tag M-1 may encode for the presence of both the allele and the polymorphic site and then electrophoresis may be used to identify the marker tag M-1.

In some embodiments, a molecular beacon may comprise the complement of the marker tag on one end and the complement of the source tag on the other end.

The method 300 of FIG. 3 continues with step 370 (f): if the source tag sharing number "d" is greater than "1," then selecting the nucleic acid samples of the identified groups from the plurality of nucleic acid samples, and repeating steps (a)-(e) at least one time with a lower source tag sharing number "d" with the selected nucleic acid samples as the plurality of nucleic acid samples, otherwise selecting the nucleic acid samples of the identified groups from the plurality of nucleic acid samples.

If there are no additional desired alleles, then the method may end here with the DNA samples of G1, G2, G4, and G5 selected (see FIG. 5A for the corresponding wells of the plates P2, P3, and P4.)

Alternatively, the method may continue with a lower source tag sharing number "d" to narrow down the number of DNA samples that include the desired alleles. For example, steps (a)-(e) could be performed with source tag sharing number "d"="1," so that only the DNA samples with the desired alleles would be selected.

Notice that in two iterations that the number of DNA samples went from "288" to "96," and then to "64."

Binning and Determining Source Tag Sharing Number "d"

The value of "d" will determine the number of nucleic acid samples that share a source tag. Source tag sharing numbers "d">1 can be advantageous when the frequency of an allele is low. For example, the Colton blood group system has a polymorphic site with two alleles: one of the alleles occurs with over 99% probability and the other allele occurs with less than 1% probability (in Caucasians). By using the same source tag code for more than one nucleic acid sample, the number of operations in selecting nucleic acid samples from a plurality of nucleic acid samples based on a set of desired alleles may be reduced for a given number of nucleic acid samples (compared with the conventional "one-sample-at-a-time" method). However, if all of the alleles are not the same for a polymorphic site, then the methods disclosed above may not unambiguously identify the alleles in step 360 (e) of the method 300 of FIG. 3 without additional disambiguation as described below.

Figure 6A:
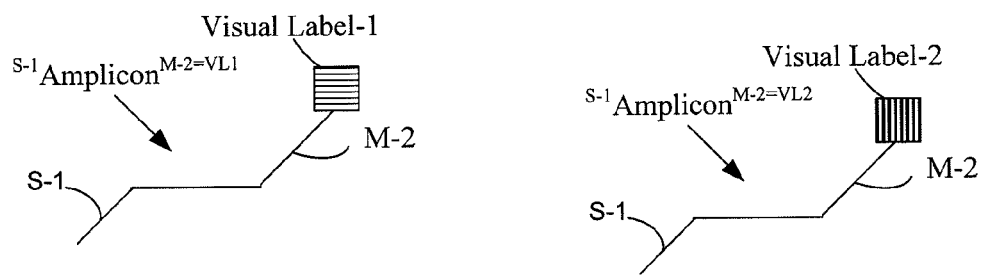
FIG. 6 schematically illustrates microparticles used to determine alleles.

FIG. 6A illustrates how an ambiguity may arise when nucleic acid samples share source tags. Illustrated in FIG. 6 are $^{S-1}$amplicons$^{M-2=VL1}$ and $^{S-1}$amplicons$^{M-2=VL2}$ which are produced from two nucleic acid samples, which for illustrative purposes will be named DNA-4 and DNA-5. It is assumed for the sake of illustration that the amplicons are produced as follows. DNA-4 is heterozygous at the polymorphic site for Colton. DNA-5 is homozygous at the polymorphic site for Colton. DNA-4 and DNA-5 were pooled, and primers with source-tag S-1 were added to the pool. Assume for the sake of illustration that PCR was performed to produce amplicons from DNA-4 and DNA-5 having the source-tag S-1, and that allele specific primers for the polymorphic site for Colton were added to the produced amplicons to produce $^{S-1}$amplicons$^{M-2=VL1}$ and $^{S-1}$amplicons$^{M-2=VL2}$. Since DNA-4 is heterozygous, both amplicons $^{S-1}$amplicons$^{M-2=VL1}$ and $^{S-1}$amplicons$^{M-2=VL2}$ are produced from DNA-4. Since DNA-5 is homozygous only one of $^{S-1}$amplicons$^{M-2=VL1}$ or $^{S-1}$amplicons$^{M-2=VL2}$ is produced from DNA-5.

Amplicons $^{S-1}$amplicons$^{M-2=VL1}$ and $^{S-1}$amplicons$^{M-2=VL2}$ are produced from the heterozygous DNA-4, reflecting the presence of both alleles, at the polymorphic site for Colton. In contrast, only $^{S-1}$amplicons$^{M-2=VL1}$ are produced from the homozygous DNA-5, reflecting the presence of only one allele at the polymorphic site for Colton.

Figure 6B:
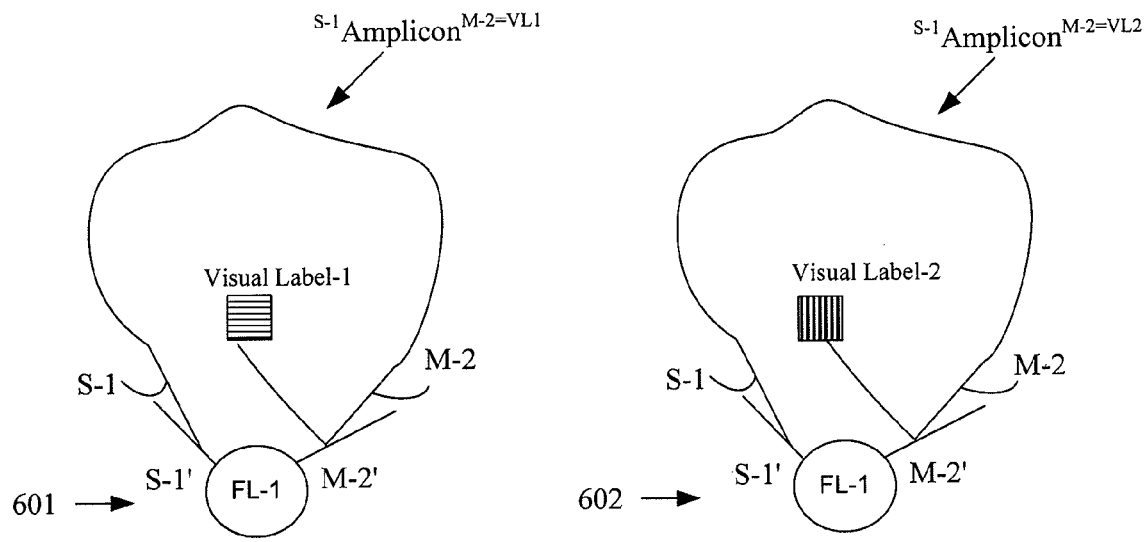

As illustrated in FIG. 6B, the signal that is recorded from a microparticle with fluorescence FL-1 having a capture probe that anneals to source tag S-1 and a capture probe that anneals to marker tag M-2 would indicate the presence of both visual label VL-1 and visual label VL-2 from the amplicons from DNA-4 and DNA-5. If amplicons were produced only from DNA-4, then the presence of both visual label VL-1 and visual label VL-2 would unambiguously signal that DNA-4 is heterozygous. But since both DNA-4 and DNA-5 share source tag S-1, the result of probing their amplicons with microparticle with fluorescence FL-1 is ambiguous because there are other possible combinations that would give the same result of both a visual marker VL-1 and visual marker VL-2. For example, DNA-4 could be homozygous for Colton (that is, have allele $Co^a$ only) and DNA-5 could be homozygous for Colton (that is, have allele $Co^b$, only); alternatively, DNA-4 could be homozygous for $Co^b$, and DNA-5 heterozygous, or DNA-4 could be homozygous for $Co^b$.

Figure 7:
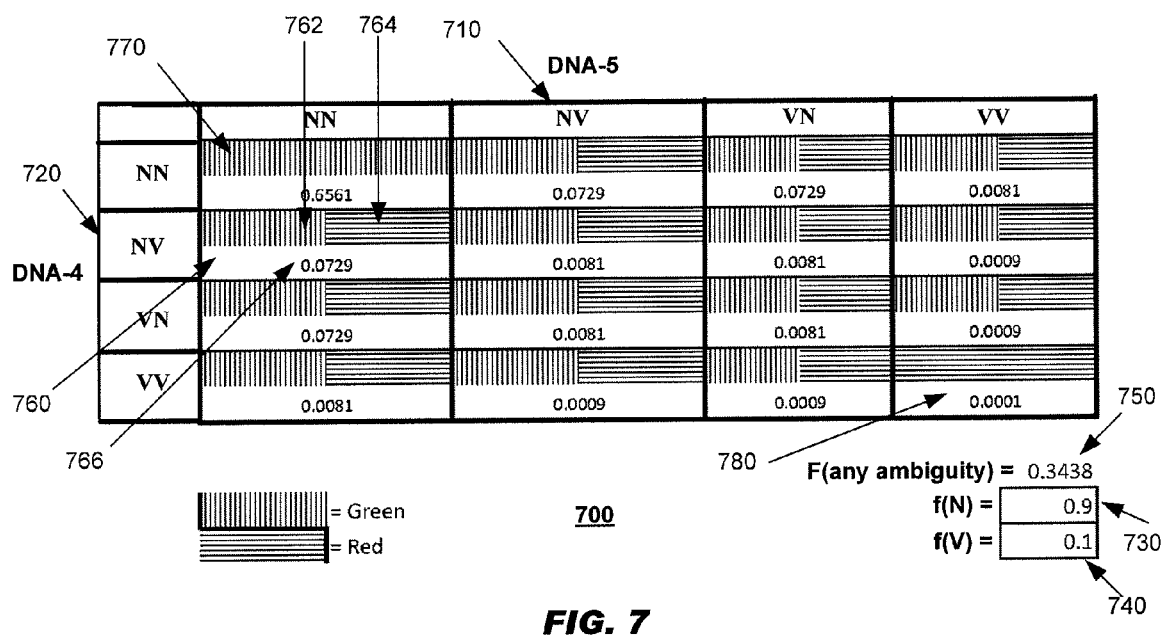
FIG. 7 schematically illustrates how an ambiguity may arise from sharing source tags in the event of heterozygosity illustrated here by DNA-4a vs. DNA-4b showing only one strand of each allele.

FIG. 7 illustrates the probabilities for an ambiguity when a source tag is shared between amplicons of two different DNA samples. Along one axis are bi-allelic configurations of the chromosomal pair for DNA-4 and along the other axis are bi-allelic configurations of the chromosomal pair for DNA-5. For purposes of illustration, only a single polymorphic site is considered.

Often the allele that has the highest probability of occurring at a polymorphic site is referred to as the normal (N) allele and the allele that has the lower probability of occurring is referred to as the variant (V) allele. The variant allele also may be referred to as "mutant" and the normal allele as "wild-type", especially for alleles known to be associated with disease.

The notation "NV" (720) means that DNA-4 is heterozygous. The two alleles are designated for illustrative purposes as "N" for normal and "V" variant; similarly, notation "NV" (710) means that DNA-5 is heterozygous; while notation "NN" indicates homozygosity for allele "N" and notation "VV" indicates homozygosity for allele "V". FIG. 6 illustrates the situation where DNA-4 is heterozygous, and DNA-5 is homozygous. The notation "f(A)=0.9" (730) in FIG. 7 means that the probability or frequency of an allele "N" is set to 90 percent. The notation "f(B)=0.1" (740) means that the probability or frequency of allele "B" is set to 10 percent. The entry (760) represents the state of the visual labels (762 and 764) and the value of the probability (766) that DNA-4 and DNA-5 have the indicated allele configuration, "NV" for DNA-4 and "NN" for DNA-5. In entry (760) one visual marker is green (762) and the other visual marker is red (764). The probability of this configuration is 0.0729 (766). The only entries in the table 700 of FIG. 7 that do not have both a red visual marker and a green visual marker are entries (770) and (780). Entry (770) corresponds to the allele configuration "NN" for both DNA-4 and DNA-5. Both visual markers are therefore green. The probability of this configuration is 0.6561 or almost ⅔ of the time, corresponding to the presence of four copies of the "N" allele (observed with probability 0.9). Hence the probability of no ambiguity is 0.9*0.9*0.9*0.9=0.6561. The other entry in Table 7 where there is no ambiguity is entry (780), where both visual markers are red, corresponding to allele configuration "VV" for both DNA-4 and DNA-5. The probability of this configuration is only 0.0001, corresponding to the presence of four copies of the "V" allele (observed with probability 0.1). Hence the probability of no ambiguity for this allele configuration ("VV" and "VV") is 0.1*0.1*0.1*0.1=0.0001.

For two nucleic acid samples sharing a source tag, the probability of an ambiguity occurring is given by Equation 1:

$$\text{Probability (ambiguity)} = 1 - f(N)^4 - f(V)^4.$$

In the example of FIG. 7, Prob(ambiguity)=1−(0.9)⁴− (0.1)⁴=−0.6561−0.0001=0.3438 (the value at 750). Similarly, the binomial theorem can be used to determine the probability of an ambiguity, for four nucleic acid samples sharing the same source tag. Let "d" be equal to the number of nucleic acid samples sharing the same source tag. In this example, "d"=4. For a bi-allelic marker: Prob(ambiguity)=1−f(n)$^{d*2}$− f(v)$^{d*2}$, or 1−f(N)⁸−f(V)⁸. The greater the number, "d", of nucleic acid samples sharing the same source tag, the greater the chance of an ambiguity. The less frequent the variant allele, the lower the probability of an ambiguity for a given value of source tag sharing number "d". In general, the probability of an ambiguity for a polymorphic site with m alleles is given by Equation (2):

$$\text{Probability (ambiguity)} = 1 - f(N)^{m*d} - f(V)^{m*d} \quad \text{Equation (2)}$$

where as above, f(N) is the frequency of a normal allele, f(V) is the frequency of a variant allele, and d is the number of samples sharing the same source tag.

The "Probability (ambiguity)" may be set to a value "C" that provides for efficiently dividing the nucleic acid samples into groups in step (a) of the method 300 in FIG. 3. Given a value of "C", a value of "d" may be determined from Equation 3. For example, "C" may be set to 50%, and if P(V)=0.01, and P(N)=0.99, then "d" would be approximately 70. The value of "d" may be lowered to the value of maximum pool size as discussed herein.

One object of a repetition of the method of FIG. 3 is to select as few nucleic acid samples as possible, which is equivalent to rejecting as many nucleic acid samples as possible, while at the same time taking advantage of the savings provided by identifying desired alleles of the nucleic acid samples together in the same pool. The value of "d" is a design parameter that may be set according to a number of parameters and experimental considerations. The parameters may include, for example, improving the speed of the selection process or the efficiency of the selection process. The experimental considerations may include the parameters and considerations such as the cost and time of performing each reaction, and the location where the experiment is performed.

Given that it is desirable to test as many nucleic acid samples together for efficiency and yet to reject as many nucleic acid samples as possible in one pass of the method, a value of "C" of 50% provides a reasonable balance, in that on average approximately 50% of the nucleic acid samples will be rejected in a repetition of the method, and still there will saving by group testing the nucleic acid samples.

Decreasing the value of "C" will result in smaller groups (less efficient testing) and rejecting greater numbers of nucleic acid samples on average, and increasing the of "C" will result in larger groups (more efficient testing), and rejecting fewer numbers of nucleic acid samples on average.

Some alleles may be determined in the same pools as other alleles. In this case, the alleles may be said to be binned in that the alleles will be determined with the same source tag sharing number. In some embodiments, alleles may be binned and different source tag sharing numbers may be used to determine the different alleles. Equation (2) would change according to the binominal theorem if more than one allele is tested in a pool.

The value of "d" may be set to the largest integer of the form 2$^n$ so that the value of Equation 2, "Probability (ambiguity)" is less than "C." Some of the more common numbers used for 2$^n$ in performing the method 300 are n=1, 2¹=2; n=2, 2²=4; n=3, 2³=8; n=4, 2⁴=16; n=5, 2⁵=32; n=6, 2⁶=64; and, n=7, 2⁷=128. The value of "d" may also be limited by a preset maximum pool size (e.g. 32), which may be related to technical reasons that limit the pool size.

In the method 300, the value "C" represents the probability that a group of nucleic acid samples includes at least one nucleic acid sample with at least one of the desired alleles.

Equation (2) can be used to derive Equation (3), which can be used to determine the maximum number of "d," given C and the frequency of the variant allele, f(V).

$$d = 0.5 * \log(1-C)/\log(1-f(V)), \quad \text{Equation (3)}$$

where preferably, as in FIG. 8, "d" is set to the largest integer of form 2$^n$ that is less than or equal to the value "d" produced by equation (3) for a preset "C".

Table 810 illustrates an arrangement of blood group system alleles 850 and their frequencies observed in African Americans. The features of table 810 include ISBT designation (element 852); polymorphic site name (element 854); the frequency of allele A (element 856); and, the frequency of allele B (element 858). The frequencies of the alleles are sometimes approximated with a "1" or "0". Two values are set prior to determining the source tag sharing number "d". These values are "C" (element 870), which, as discussed above, is the highest acceptable probability of an ambiguity occurring in a plurality of "d" nucleic samples. Additionally, the maximum pool size abbreviated as "Max PoolSz" (element 872) is set prior to determining the source tag sharing numbers "d". The "Max PoolSz" (element 872) may be determined by limitations arising from the steps of the method. For example, in some embodiments, two microparticles with different tags are added to a pool to identify alleles of a single nucleic acid sample. Thus, the number of nucleic acid samples that are pooled together is limited by the number of different microparticle tags that can be manufactured.

The minimum frequency of the allele with the lowest frequency is represented as "f" (element 860). A "d(S)" (element 862) is calculated using Equation 3 with C=0.1800 (element 870) (which is 18%). The logarithm to the base 2 (element 864) is calculated for each of the "d(S)" values (element 862) and rounded down to the nearest whole integer. The number "2" is then raised to the logarithm to the base 2 (element 864) which yields the number of samples "d" to use for the source tag sharing number of method 200 (element 866) where "d" is of the form 2^n for n an integer such that equation 2 "Probability (ambiguity)" is less than C (18%) 870. The value in column (element 866) is reduced to the max pool size (element 872) which is 32 in the present example. For example, the calculated "N" (element 862) for allele "CO" (element 854) is 99.1758, and the closest power of 2 less than 99.1758 is 64. But since 64 is greater the "Max PoolSz" (element 872), the "Max PoolSz", which is 32, is used for the source tag sharing number "d" of method 300 of FIG. 3.

Table 820 illustrates the alleles from table 810 binned into the source tag sharing "d" number, which is the number of source samples that may share the same source tag. For example, "SC" (element 854) is placed into a bin with a source tag sharing number "d"=32 because its value for "d", shown, in column (element 866) is 32. The number of bins illustrated in table 820 is 6, for "d" of 1, 2, 4, 8, 16, and 32, which is all the bins that are possible for powers of 2 that do not exceed 32. The total number of alleles (element 876) is listed for each of the bins. Alleles that have the same source tag sharing number "d" may be identified in the same pool. Alleles that are identified in the same pool may be said to be binned together.

Similarly, tables 830 and 840 illustrate the source tag sharing numbers "d" and allele binning for Caucasians. Note the difference in the frequencies at the polymorphic sites (850) between the two groups. For example, the variant form of allele SC (854; Scianna blood group system) has a frequency of 0.006 in Caucasians and only 0.002 in African Americans, which results in SC being in the 32 bin for African Americans, but in the 16 bin for Caucasians.

The seven polymorphic sites of table 820 with a "d" value of 1 (see FIG. 8A, for polymorphic sites "FY, GYPBS, GATA, DO-793, GYPA, JK, HbS173") may be binned together in the method 300 of FIG. 3. The alleles of the seven polymorphic sites listed above may be said to be "binned" together.

For source tag sharing number "d"=2, alleles associated with the three polymorphic sites that are binned together are ("LU, DO-323, and DO-350").

For source tag sharing number "d"=8, Alleles associated with the two polymorphic sites binned together ("K(1/2), FY265") are binned together.

For "d"=32, alleles associated with the four polymorphic sites are binned together ("SC, DI(B/A), CO, and LW").

In some embodiments, one or more alleles with a determined source tag sharing number "d" may be binned into a lower source tag sharing number "d". For example, a source tag sharing number of "8" was determined for the K(1/2) of FIG. 8A. However, if K(1/2) was to be determined with DO-323, which was determined to have a source tag sharing number of 2, and no other alleles were to be determined, then a source tag sharing number of "d"=2 may be used for K(1/2) so that the method could be performed to determine K(1/2) and DO-323 in the same wells.

In some embodiments, instead of microparticles being added to the wells, a set of pre-assembled planar arrays of encoded microparticles may be used to identify alleles in method 300. Aliquots of the products of the identifying step 360 of method 300 may be transferred from the wells of plate P5 to positions, in this case, containing a pre-assembled planar array of encoded microparticles.

In some embodiments, electrophoresis may be used to identify the alleles. The design of the source and marker tags to enable identification with electrophoresis is discussed in more detail below.

In some embodiments, step 350 (d) of method 300 of FIG. 3 may be performed by contacting the amplicons in the pooling container for the source tag sharing number "d" with an allele-specific hybridization probe comprising a marker tag for identifying the allele to produce an allele-specific hybridization products, said allele-specific products comprising said marker tag and said source tag.

In some embodiments, the number of alleles at the polymorphic site is greater than two.

In some embodiments, the source tags need only be unique for DNA samples that are present in the same pool.

Some embodiments have the advantage of reducing the number of extraction and amplification operations when the source tag sharing number "d" is greater than 1. Additionally, the number of discrimination and detection operations is reduced from the traditional method, which takes the number of samples for which the desired attributes is to be determined.

Some embodiments of the invention have the advantage of increasing the rate of "throughput" of allele determination by selecting only those groups of nucleic acids that include at least one nucleic acid that has at least one of the desired alleles. Source tag sharing between even 2 or 4 samples produces a significant reduction in the number of individual DNA extractions and amplification steps, while reducing the complexity.

The method described may have the advantage that it may be difficult to perform amplification for different polymorphisms, either at the same time or sequentially, because the parameters such as temperature and the contents of the well may vary depending on the polymorphism.

In some embodiments of the invention, the identifying step 360 of method 300 is performed using microparticles comprising a complement source tag capture probe and a complement marker tag capture probe that is coded for both an allele and a specific polymorphic site. This embodiment is discussed above. One advantage of this embodiment is that the microparticles may be used in multiple wells or pools in the identifying step, since the source tags and the marker tags may be shared between separate pools or wells.

Figure 9:
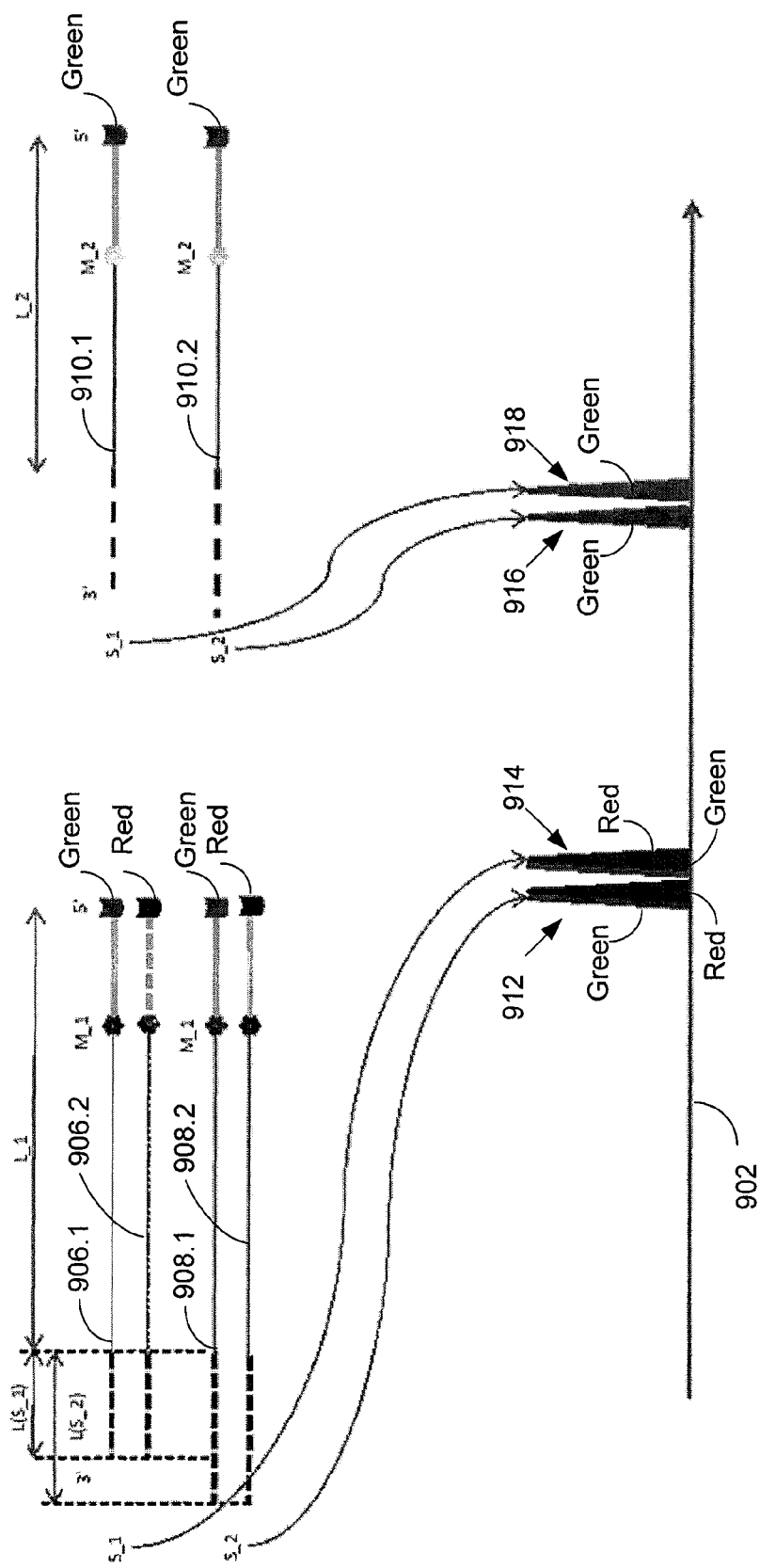
FIG. 9 schematically illustrates detection of products comprising specific combinations of source tags and marker tags by capillary electrophoresis.

In some embodiments of the invention, detection of hybridization or amplification products comprising source tags and marker tags may be accomplished by capillary electrophoresis, as illustrated in FIG. 9. Illustrated in FIG. 9 are six amplification products each comprising a source tag, labeled as either S__1 or S__2, and a marker tag, labeled as either M__1 or M__2. As illustrated, the differential electrophoretic mobility of amplicons of different length places a longer polynucleotide more to the left along the axis 902 and the shorter polynucleotide more to the right. As illustrated, the amplicons 906, 908, 910 comprise a fluorescent tag (red or green) so that the position along the axis 902 can then be used to determine source tags and polymorphic sites. As illustrated the marker tags are the same length and the marker tag are distinguished by color, but different length marker tags could be used to distinguish between marker tags.

Since the total nucleotide sequence length (plus fluorescent tag) will determine where along the axis 902 the fluorescence from the fluorescent tag can be detected, the following illustrates how to design hybridization or amplification products to enable them to be identified using electrophoretic separation.

In some embodiments, polymorphic sites may be distinguished by designing pairs of primers that produce different lengths of amplicons that include the polymorphic site that is being interrogated. For example, in FIG. 9, 906.1, 906.2, 908.1, and 908.2 are all of the same length (number of nucleotides plus marker tag) L__1. So, this length L__1 may be used to identify one polymorphic site. Then a different length, L__2, may be used for 910.1 and 910.2 to identify a second polymorphic site. As illustrated in FIG. 9, 910.1 and 910.2 are separated to the right of 906 and 908 due to the smaller size of L__2 compared with L__1. In one embodiment, no additional marker tag is used (that is, the length of the marker tag is zero), as no sequence-specific capture is required for electrophoretic detection.

The different source tags can then be distinguished by using different lengths for different source tags. As illustrated, S__1 is shorter than S__2 so the hybridization or amplification products including S__1 are to the right of the hybridization or amplification products that are the same except for comprising S__2. For example, 910.1 and 910.2 may represent the hybridization or amplification products for one allele determination from two different source samples. Both, 910.1 and 910.2 are green so for the purposes of this example we can assume that 910.1 and 910.2 indicate that the nucleic acid sample labeled with S__1 and S__2 has the Normal allele for the polymorphic site that is encoded with length L__2.

Illustrated in FIG. 9 is also 906.1 and 906.2 which are hybridization or amplification products with a length L__1 that encodes a different polymorphic site than L__2. In this case, since both 906.1 and 906.2 are generated, at least one of the nucleic acid samples encoded with S__1 is heterozygous for the polymorphic site encoded by L__1. Note that both the green and red signal can be distinguished at 914.

Thus, by choice of amplicon length and source tag length, electrophoretic separation may be used to identify alleles for multiple source tags and for multiple polymorphic sites.

A number of other techniques are available for nucleic acid analysis based upon nucleic acid length. One such method is denaturing gradient gel electrophoresis.

In some embodiments, source tags also may be modified to display "drag" tags to modulate electrophoretic mobility. For example, see Won et al., "Electrophoresis", 26(11):2138-2148 (2005), the entire disclosure of which is incorporated herein by reference. In some embodiments, the marker tags may vary in length to encode source tag, polymorphic site, and allele. For example, a shorter marker tag with a green fluoresce may indicate the normal allele, and a longer maker tag with a green fluoresce may indicate the variant allele.

In some embodiments, allele-specific second reaction products are interrogated by differential melting curve analysis.

Figure 10:
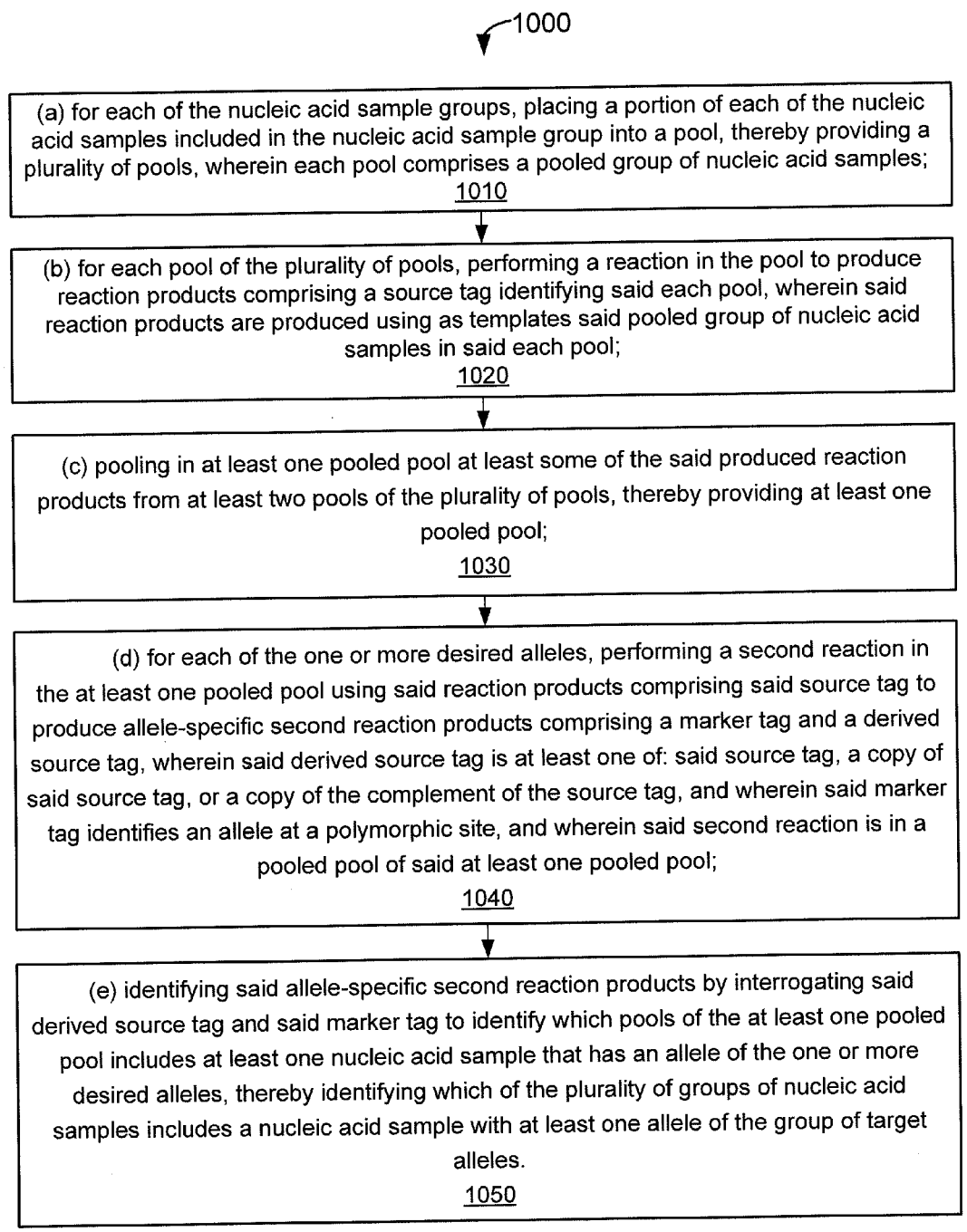
FIG. 10 schematically illustrates an alternative method of selecting nucleic acid samples from a plurality of nucleic acid samples based on one or more desired attributes.

FIG. 10 schematically illustrates an alternative embodiment for a method 1000 of identifying which groups of a plurality of groups of nucleic acid samples includes a nucleic acid sample with at least one allele of one or more desired alleles. The method 1000 may optionally begin with generating the plurality of nucleic acid sample groups by dividing a plurality of nucleic acid samples into nucleic acid sample groups, each group containing approximately "d" nucleic acid samples so that each nucleic acid sample of the plurality of nucleic acid samples is included in at least one group, where "d" is a number determined based on a frequency of the one or more desired alleles. For example, as discussed above, FIG. 5A illustrates dividing "96" DNA samples (element 514) into groups G1, G2, G3, G4, G5, G6 of "16" DNA samples each. Note that the maximum pool size (element 510) is "32," and that alleles SCII and $DI^b$ (element 516) are still the desired attributes.

The method continues with step 1010 (*a*): for each of the nucleic acid sample groups, placing a portion of each of the nucleic acid samples included in the nucleic acid sample group into a pool, thereby providing a plurality of pools, wherein each pool comprises a pooled group of nucleic acid samples. For example, as discussed above, referring to FIG. 5A, a pipette is used to place a portion of the DNA samples from wells w1 to w16 of plate P2 (refer to FIG. 4A for well numbering) into well w2 of plate P5 to form a pool comprising group G1 of DNA samples. Similarly, groups pools comprising G2 through G6 DNA samples are formed in wells w10, w18, w26, w34, and w42 respectively of P5.

The method continues with step 1020 (*b*): for each pool of the plurality of pools, performing a reaction in the pool to produce reaction products comprising a source tag identifying said each pool, wherein said reaction products are produced using as templates said pooled group of nucleic acid samples in said each pool.

For example, as discussed above, in one or more embodiments step 1020 (*b*) comprises for each pool of the plurality of pools amplifying the nucleic acid samples in the pool with primers comprising a source tag to produce amplicons comprising said source tag identifying said each pool, where said amplicons are produced using as templates said pooled group of nucleic acid samples in said each pool. Amplification may be performed by conventional methods of nucleic acid amplification, e.g., polymerase chain reaction (PCR).

The amplification is now described in greater detail. FIG. 5B illustrates well "w2" with DNA sample "1" through "16" pooled together prior to step (c). FIG. 5C illustrates a primer with source-tag s2 identifying well "w2". Primers with source-tag s2, which may be represented as $^{s-2}$primer, are placed in well "w2" and primers with source-tags identifying the other wells, $^{s-10}$primer, $^{s-18}$primer, $^{s-26}$primer, $^{s-34}$primer, and $^{s-42}$primer are placed in the other wells w10, w18, w26, w34, and w42 of plate P5.

The method continues with step 1030 (*c*): pooling in at least one pooled pool at least some of the said produced reaction products from at least two pools of the plurality of pools, thereby providing at least one pooled pool.

For example, as discussed above, continuing with the example of FIG. 5, as illustrated in FIG. 5E, a pipette is used to pool together wells "w2" (G1) and "w10" (G2) into well "w3" (see FIG. 4A for well numbering), to pool together wells "w18" (G3) and "w26" (G4) into well "w11", and to pool together wells "w34" (G5) and "w42" (G6) into well "w19." After the pooling, well "w3" comprises $^{S-2}$amplicons and $^{S-10}$amplicons, well "w11" comprises $^{S-18}$amplicons and $^{S-26}$amplicons, and well "w19" comprises $^{S-34}$amplicons and $^{S-42}$amplicons.

The method continues with step 1040 (*d*): for each of the one or more desired alleles, performing a second reaction in the at least one pooled pool using said reaction products comprising said source tag to produce allele-specific second reaction products comprising a marker tag and a derived source tag, wherein said derived source tag is at least one of: said source tag, a copy of said source tag, or a copy of the complement of the source tag, and wherein said marker tag identifies an allele at a polymorphic site, and wherein said second reaction is in a pooled pool of said at least one pooled pool.

As discussed above, for example, allele-specific primers directed to the polymorphisms SCI69 and DI2561 are added to wells w3, w11, and w19 (see the well numbering scheme of FIG. 4A) of plate P5. The samples in wells w3, w11 and w19 are then amplified by, for example, using PCR with the DNA samples in the wells being used as a template, so that if a DNA sample contains an allele, then an amplicon is produced with a marker tag identifying the allele.

The method continues with step 1050 (*e*): identifying said allele-specific second reaction products by interrogating said derived source tag and said marker tag to identify which pools of the at least one pooled pool includes at least one nucleic acid sample that has an allele of the one or more desired alleles, thereby identifying which of the plurality of groups of nucleic acid samples includes a nucleic acid sample with at least one allele of the one or more desired alleles.

For example, as discussed above, FIG. 5G illustrates how some embodiments identify allele specific second reaction products for well "w3" which contains "16" DNA samples from each of wells "w2" and "w10". Four types of microparticles 501, 502, 503, 504, are added to well "w3". The microparticles comprise capture probes M-1' or M-2' and S2' or S10'. The microparticles also comprise a fluorescent label "F-1", "F-2", "F-3", "F-4," respectively, that identifies the microparticle.

The second reaction products may be identified because they anneal to complementary capture probes on the microparticles 501, 502, 503, 504, and the marker tags on the second reaction products comprise fluorescent labels which can be used to determine which allele is at the polymorphic site.

Thus, which of the groups include at least one DNA sample with at least one desired allele can identified.

Figure 11:
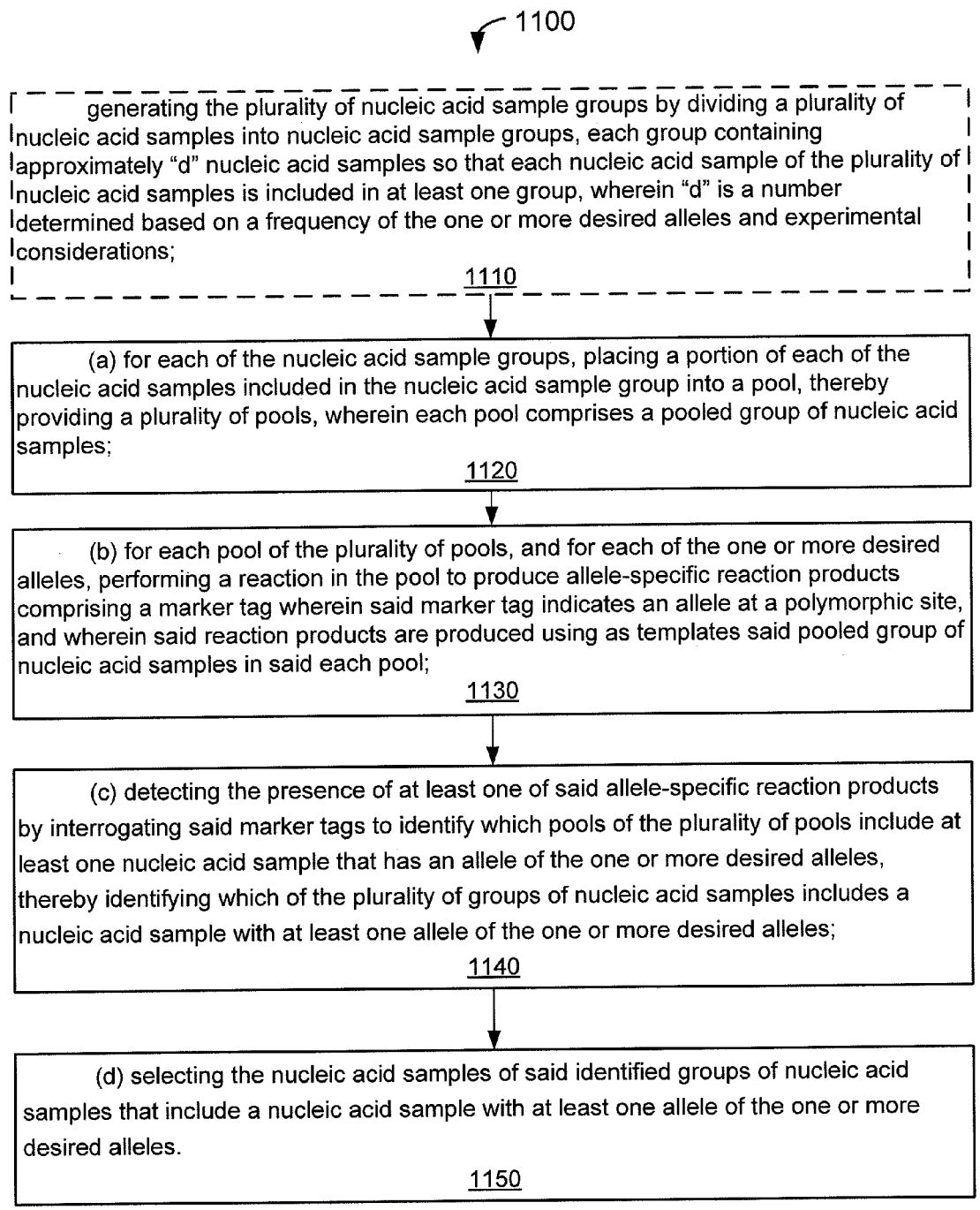
FIG. 11 schematically illustrates an alternative embodiment for a method of selecting nucleic acid samples from groups of a plurality of groups of nucleic acid samples.

FIG. 11 schematically illustrates an alternative embodiment for a method 1100 of selecting nucleic acid samples from groups of a plurality of groups of nucleic acid samples.

The method 1100 of FIG. 11 may optionally begin with a step 1110 of generating the plurality of nucleic acid sample groups by dividing a plurality of nucleic acid samples into nucleic acid sample groups, each group containing approximately "d" nucleic acid samples so that each nucleic acid sample of the plurality of nucleic acid samples is included in at least one group, wherein "d" is a number determined based on a frequency of the one or more desired alleles and experimental considerations. For example, as discussed above, FIG. 4B illustrates dividing "288" DNA samples (element 414) into groups G1, G2, G3, G4, G5, G6, G7, G8, G9 of "32" DNA samples each. The experimental considerations are discussed above.

The method 1100 of FIG. 11 continues with step 1120 (a) for each of the nucleic acid sample groups, placing a portion of each of the nucleic acid samples included in the nucleic acid sample group into a pool, thereby providing a plurality of pools, wherein each pool comprises a pooled group of nucleic acid samples. For example, as discussed above with regards to FIG. 4B, a pipette is used to place a portion of the DNA samples from wells w1 to w32 of plate P2 into well w1 of plate P5 to form a pool comprising group G1 of DNA samples. Similarly, pools comprising groups G2 through G9 of DNA samples are formed.

The method 1100 of FIG. 11 continues with step 1130 (b) for each pool of the plurality of pools, and for each of the one or more desired alleles, performing a reaction in the pool to produce allele-specific reaction products comprising a marker tag wherein said marker tag indicates an allele at a polymorphic site, and wherein said reaction products are produced using as templates said pooled group of nucleic acid samples in said each pool.

For example, as discussed above in regards to step 350 (d) of method 300 of FIG. 300, FIG. 4C illustrates well "w1" of plate P5 (FIG. 4B) with "32" DNA samples, DNA-1, DNA-2, . . . , DNA-32. Allele-specific primers directed to the polymorphisms SCI69 and DI2561 are added to wells w1, w9, w17, w25, w33, w41, w49, w57, and w65 (see the well numbering scheme of FIG. 4A) of plate P5. For example, FIG. 4D illustrates allele-specific primers, primer$^{M-1=VL1}$, primer$^{M-1=VL2}$, primer$^{M-2=VL1}$, primer$^{M-2=VL2}$. Primer$^{M-1=VL1}$ is an allele-specific primer for SCI, primer$^{M-1=VL2}$ is an allele-specific primer for SCII, primer$^{M-2=VL1}$ is an allele-specific primer for DI$^a$, and primer$^{M-2=VL2}$ is an allele-specific primer for DI$^b$. The primers include either M-1 or M-2, which are unique oligonucleotide tags, and either VL1 or VL2, which are visual labels. The combination of a unique oligonucleotide tag with a visual label is the marker tag in this case and provides enough information to identify the allele.

The samples in wells w1, w9, w17, w25, w33, w41, w49, w57, and w65 are then amplified, for example using PCR with the DNA samples in the wells being used as a template, so that if a DNA sample contains an allele, then an amplicon is produced with a marker tag identifying the allele. FIG. 4E illustrates the four types of amplicons that could be produced as a result of the amplification. Amplicon$^{M-1=VL2}$ would be produced from primer$^{M-1=VL1}$ and a DNA sample with allele SCI, amplicon$^{M-1=VL2}$ would be produced from primer$^{M-1=VL2}$ and a DNA sample with allele SCII, amplicon$^{M-2=VL1}$ would be produced from primer$^{M-2=VL1}$ and a DNA sample with allele DI$^a$, and amplicon$^{M-2=VL2}$ would be produced from primer$^{M-2=VL2}$ and a DNA sample with allele DI$^b$.

The method 1100 of FIG. 11 continues with step 1140 (c) of detecting the presence of at least one of said allele-specific reaction products by interrogating said marker tags to identify which pools of the plurality of pools include at least one nucleic acid sample that has an allele of the one or more desired alleles, thereby identifying which of the plurality of groups of nucleic acid samples includes a nucleic acid sample with at least one allele of the one or more desired alleles.

For example, as discussed above with regards to FIG. 4, allele-specific reaction products may be interrogated by microparticle-mediated allele identification. For the example, illustrated in FIG. 4, visual label "VL1" is detected near fluorescent labels "FL-1" and "FL-2" in all of the groups G1, . . . , G9 (FIG. 4B.) This result identifies that all of the groups G1, . . . , G9 include one or more DNA samples that have alleles SCI and DI$^a$, but does not identify which of the DNA samples specifically have alleles SCI and DI$^a$. Only if no visual label V2 is detected in a group can the alleles for all the samples in the group be unambiguously identified.

Visual label "VL2" is detected near fluorescent label "FL-1" only in groups G1 (w1), G4 (w25), and G8 (w57). See FIG. 4B which matches wells to groups. This result indicates that groups G1, G4, and G8 include one or more DNA samples that have alleles SCII, thereby identifying which of the plurality of groups of nucleic acid samples includes a nucleic acid sample with at least at least one desired allele. But this result does not identify which of the DNA samples specifically have allele SCII. Visual label "VL2" is detected near fluorescent label "FL-2" only in groups G1 and G8. This result indicates that groups G1 and G8 include one or more DNA samples that have allele DI$^b$, thereby identifying which of the plurality of groups of nucleic acid samples includes a nucleic acid sample with at least at least one desired allele. But again, this result does not identify which of the DNA samples specifically have DI$^b$. The groups G1, G4, and G8, have then been identified as having at least one nucleic acid sample with one or more of the desired alleles SCII and DI$^b$.

The method 1100 of FIG. 11 continues with step 1150 (d) of selecting the nucleic acid samples of said identified groups of nucleic acid samples that include a nucleic acid sample with at least one allele of the one or more desired alleles.

For example, as discussed above with regards to FIG. 4, the nucleic acid samples of groups G1, G4, and G8 are selected as including at least one of the desired alleles SCII or DI$^b$.

Thus, the nucleic acid samples of groups with one or more desired alleles have been selected from a plurality of groups of nucleic acid samples.

In some embodiments, the method 1100 of FIG. 11 further comprises after step (d) a step of repeating steps (a)-(d) with one or more additional alleles as the one or more desired alleles.

For example, the method may be repeated with K(1/2) and FY265 as the desired alleles. In some embodiments, the plurality of groups of nucleic acid samples are the groups selected in step (d), which in the example above are G1, G4, and G8.

The term "selecting" is used in a broad sense to include identifying nucleic acid samples. For example, a laboratory may perform the test described herein and not explicitly select nucleic acid samples, but may generate test results that enable another party to select nucleic acid samples based on the test results that identify nucleic acid samples.

In some embodiments, the method of the invention can be used to select nucleic acid samples from a plurality of nucleic acid samples based on desired alleles comprising epigenetic modifications. Nucleic acid samples comprising single-stranded DNA are first treated with sodium bisulfite to convert non-methylated cytosine residues to uracil residues. The bisulfite-treated sample is then subject to analysis as described above. Methods for bisulfite conversion of non-methylated cystosine residues and subsequent methylation-specific PCR are described, for example, by Herman et al., Proc. Natl. Acad. Sci USA, 93(18):9821-9826 (1996), the entire disclosure of which is incorporated herein by reference.

In some embodiments of the method, where the source tag sharing number "d" determined for at least one desired allele is equal to maximum pool size, the method comprises identifying at least two alleles wherein there is at least one desired allele for which the source tag sharing number "d" is determined to be less than maximum pool size.

In some embodiments of the method, where the source tag sharing number "d" determined for at least one desired allele is equal to "1", the method comprises selecting nucleic acid samples based on at least two desired alleles, wherein there is at least one desired allele for which the source tag sharing number "d" is determined to be greater than "1."

In some embodiments of the method, the method comprises selecting nucleic acid samples based on at least two desired alleles, wherein the source tag sharing number "d" for a first desired allele is different from the source tag sharing number "d" for the at least second desired allele, and the source tag sharing number "d" is determined based on the frequency of the allele.

In some embodiments of the method, the method is practiced only with desired alleles for which source tag sharing number "d" is less than maximum pool size.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

Although described in connection with preferred embodiments thereof, it will be appreciated by those skilled in the art that additions, deletions, modifications, and substitutions not specifically described may be made without departure from the spirit and scope of the invention as defined in the appended claims.

What is claimed is:

1. A method of selecting nucleic acid samples from a plurality of nucleic acid samples based on one or more desired alleles at one or more polymorphic sites, the method comprising:

(A) setting a user-set value C based on the testing efficiency desired by the user to a value between 0 and 1, but not equal to 0 or 1;

(B) calculating for each desired allele a value "d," wherein "d" is a positive integer determined by the user-set value C and the frequency of the desired allele in a population of individuals;

(C) grouping into mathematical bins one or more of said desired alleles, wherein all alleles in a mathematical bin have the same value for "d";

(D) determining a value for the maximum pool size, wherein the maximum pool size is the maximum number of samples in a pool, wherein the value is a number greater than one and is based on technical limitations of performing the steps of the herein method of identifying alleles;

(E) selecting one bin from the mathematical bins of alleles determined in step (C) with the proviso that if "d" for the selected bin is greater than the maximum pool size determined in step (D), then "d" for the bin is set to the maximum pool size;

(F) collecting aliquots from "d" number of nucleic acid samples of said plurality of nucleic acid samples, and combining said aliquots to form at least one nucleic acid sample pool, wherein each nucleic acid sample pool contains exactly "d" aliquots;

(G) (i) performing a reaction in each nucleic acid sample pool to produce reaction products comprising (a) polymorphic site(s) comprising the allele(s) of the selected bin and (b) a source tag identifying each pool, wherein said reaction products are produced using as templates said nucleic acid samples in each said pool;

(ii) if "d" is less than the maximum pool size, then forming at least one pooled pool comprising at least some of the reaction products from a number of pools, said number of pools determined as the result of dividing the maximum pool size by "d"; wherein if said number of pools is not an integer, then said number of pools is set to the closest lesser positive integer;

(iii) if "d" is equal to the maximum pool size, then proceeding to step (H) without forming pooled pools;

(H) for each of the alleles of the one or more desired alleles, performing a second reaction in the at least one pool or pooled pool using said reaction products comprising said source tag to produce allele-specific second reaction products comprising a marker tag, wherein said marker tag identifies an allele at a polymorphic site;

(I) interrogating said marker tags;

(J) (i) if all marker tags in a pool or pooled pool are identical and, if said marker tags correspond to the one or more desired alleles, then selecting the nucleic acid samples in said pool or pooled pool as being homozygous for said allele of the one or more desired alleles; or (ii) if all marker tags in a pool or pooled pool are identical, and if said marker tags do not correspond to the one or more desired alleles, then optionally eliminating from consideration the nucleic acid samples in said pool or pooled pool; or (iii) if all marker tags in a pool or pooled pool are not identical, then:

(a) interrogating the source tags of the second reaction products in said pool or pooled pool to determine which nucleic acid samples were placed into that pool or pooled pool;

(b) identifying the marker tags of the second reaction products in said pool or pooled pool; and (c) if said pool or pooled pool comprises a second reaction product with at least one marker tag corresponding to an allele of the one or more desired alleles, then selecting the nucleic acid samples in said pool or pooled pool as containing at least one copy of an allele of the one or more desired alleles.

2. The method of selecting nucleic acid samples of claim 1, wherein in step (G) (i) performing a reaction in a pool comprises: amplifying the nucleic acid samples in the pool with primers comprising a source tag, and wherein said reaction products comprise amplicons.

3. The method of selecting nucleic acid samples of claim 2, wherein said amplifying the nucleic acid samples comprises amplifying the nucleic acid samples by performing a polymerase chain reaction (PCR).

4. The method of selecting nucleic acid samples of claim 1, wherein in step (H) performing a second reaction comprises:
amplifying said reaction products with allele-specific primers using said reaction products as templates, and wherein said allele-specific second reaction products comprise allele-specific amplicons.

5. The method of selecting nucleic acid samples of claim 4, wherein said allele-specific amplicons indicate the identity of the allele of the allele-specific amplicon by a dye color or by a length of the allele-specific amplicon.

6. The method of selecting nucleic acid samples of claim 5, wherein said amplifying the nucleic acid samples comprises amplifying the nucleic acid samples by performing a polymerase chain reaction (PCR).

7. The method of selecting nucleic acid samples of claim 1, wherein said marker tag of said second reaction products comprises at least one of the following to identify an allele: an oligonucleotide tag or a fluorescent tag.

8. The method of selecting nucleic acid samples of claim 1, wherein said marker tag comprises an oligonucleotide tag comprising a first nucleotide sequence to identify an allele and a second nucleotide sequence to identify a polymorphic site.

9. The method of selecting nucleic acid samples of claim 8, wherein said oligonucleotide tag comprises a nucleotide sequence to identify both a polymorphic site and said allele.

10. The method of selecting nucleic acid samples of claim 1, wherein said marker tag of said second reaction products comprises at least one of the following to identify a polymorphic site of a plurality of polymorphic sites where the one or more desired alleles is located: an oligonucleotide tag or a fluorescent tag.

11. The method of selecting nucleic acid samples of claim 1, wherein interrogating comprises:
interrogating said source tag and said marker tag of said second reaction products by contacting said second reaction products with micro-particles, said micro-particles comprising a first capture probe complementary to said source tag and comprising an optical tag that identifies said micro-particle.

12. The method of selecting nucleic acid samples of claim 11, wherein said micro-particles further comprise a second capture probe complementary to said marker tag, and wherein said marker tag is an oligonucleotide tag.

13. The method of selecting nucleic acid samples of claim 11, wherein said marker tag comprises an optical tag.

14. The method of selecting nucleic acid samples of claim 13, wherein said optical tag is a fluorescent tag.

15. The method of selecting nucleic acid samples of claim 1, wherein in step (I) or (J) interrogating said source tag or said marker tag comprises:
interrogating said source tag or said marker tag of said second reaction products by electrophoretic separation of said second reaction products.

16. The method of selecting nucleic acid samples of claim 15, wherein the interrogating comprises determining a length of the second reaction products by electrophoretic separation.

17. The method of identifying alleles of claim 15, wherein said marker tag comprises an optical tag.

18. The method of selecting nucleic acid samples of claim 15, wherein the source tag identifying said each pool or pooled pool identifies said each pool or pooled pool by a length of the source tag.

19. The method of selecting nucleic acid samples of claim 16, wherein the marker tag identifies an identity of a polymorphic site by a length of the marker tag.

20. The method of selecting nucleic acid samples of claim 15, wherein the identity of a polymorphic site is identified by the total length of said second reaction products.

21. The method of selecting nucleic acid samples of claim 1, wherein said source tag is a sequence of nucleotides selected such that the sequence does not duplicate a naturally occurring sequence in the genome of the organism under study.

22. The method of selecting nucleic acid samples of claim 1, wherein said marker tag uniquely identifies an allele at a polymorphic site.

23. The method of claim 1 wherein "d" is determined using the following formula:

$$d=0.5*\log(1-C)/\log(1-f(V));$$

wherein f(V) is the frequency of a desired allele and has a value between 0 and 1, but not equal to 0 or 1, wherein if the value of "d" is not a natural number of the form $2^n$, wherein n is a non-negative integer, then "d" is set to the nearest natural number of the form $2^n$ that is less than "d".

24. The method of claim 1 wherein the value of "d" is set to the closest integer less than or equal to the maximum pool size.

25. The method of claim 1 further comprising repeating steps (A)-(J) as needed with one or more additional alleles as the one or more desired alleles.

26. The method of claim 1 wherein in step (I) interrogating said marker tag comprises:
interrogating said marker tag of said second reaction products by melting curve analysis of said second reaction products.

27. The method of selecting nucleic acid samples of claim 1, wherein the marker tag identifies the identity of a polymorphic site by a color of the marker tag.

28. The method of claim 1 further comprising:
(K) repeating step (E)-(K) for one or more additional mathematical bins selected from the mathematical bins of alleles determined in step (C), wherein the performance of steps (E)-(J) for a mathematical bin may be performed concurrent with, prior to, or subsequent to performance of step (E)-(J) for any other mathematical bin.

29. A method of selecting nucleic acid samples from a plurality of nucleic acid samples based on one or more desired alleles at one or more polymorphic sites, the method comprising:

(A) setting a user-set value C based on the testing efficiency desired by the user to a value between 0 and 1, but not equal to 0 or 1;
(B) calculating for each desired allele a value "d," wherein "d" is a positive integer determined by the user-set value C and the frequency of the desired allele in a population of individuals;
(C) grouping into mathematical bins one or more of said desired alleles, wherein all alleles in a mathematical bin have the same value for "d";
(D) determining a value for the maximum pool size, wherein the maximum pool size is the maximum number of samples in a pool, wherein the value is a number greater than one and is based on technical limitations of performing the steps of the herein method of identifying alleles;
(E) selecting one bin from the mathematical bins of alleles determined in step (C) with the proviso that if "d" for the selected bin is greater than the maximum pool size determined in step (D), then "d" for the bin is set to the maximum pool size;
(F) collecting aliquots from "d" number of nucleic acid samples of said plurality of nucleic acid samples, and combining said aliquots to form at least one nucleic acid sample pool, wherein each nucleic acid sample pool contains exactly "d" aliquots;
(G) (i) performing a reaction in each nucleic acid sample pool to produce reaction products comprising (a) polymorphic site(s) comprising the allele(s) of the selected bin and (b) a source tag identifying each pool, wherein said reaction products are produced using as templates said nucleic acid samples in each said pool;
   (ii) if "d" is less than the maximum pool size, then forming at least one pooled pool comprising at least some of the reaction products from a number of pools, said number of pools determined as the result of dividing the maximum pool size by "d"; wherein if said number of pools is not an integer, then said number of pools is set to the closest lesser positive integer;
   (iii) if "d" is equal to the maximum pool size, then proceeding to step (H) without forming pooled pools;
(H) for each of the alleles of the one or more desired alleles, performing a second reaction in the at least one pool or pooled pool using said reaction products comprising said source tag to produce allele-specific second reaction products comprising a marker tag, wherein said marker tag identifies an allele at a polymorphic site;
(I) contacting said second reaction products with micro-particles comprising a first capture probe complementary to said source tag and a second capture probe complementary to said marker tag and an optical tag identifying each combination of first and second capture probes displayed on said micro-particle; and
(J) capturing desired second reaction products having a source tag and a marker tag identifying a desired allele that is bound to at least one said micro-particle, thereby selecting said desired second reaction products.

30. The method of claim 29 further comprising:
(K) repeating step (E)-(K) for one or more additional mathematical bins selected from the mathematical bins of alleles determined in step (C), wherein the performance of steps (E)-(J) for a mathematical bin may be performed concurrent with, prior to, or subsequent to performance of step (E)-(J) for any other mathematical bin.

\* \* \* \* \*